United States Patent [19]
Diaz et al.

[11] Patent Number: 6,030,952
[45] Date of Patent: Feb. 29, 2000

[54] BENZOFURAN-ACRYLIC ACID DERIVATIVES AND THEIR USE AS MODULATORS OF RXRS OR RARS RECEPTORS

[75] Inventors: Philippe Diaz, Nice; Bruno Charpentier, Biot, both of France

[73] Assignee: Centre International de Recherches Dermatologioues galderma, Valbonne, France

[21] Appl. No.: 09/117,696

[22] PCT Filed: Dec. 4, 1997

[86] PCT No.: PCT/FR97/02205

§ 371 Date: Oct. 13, 1998

§ 102(e) Date: Oct. 13, 1998

[87] PCT Pub. No.: WO98/24778

PCT Pub. Date: Jun. 11, 1998

[30] Foreign Application Priority Data

Dec. 4, 1996 [FR] France ................... 96 14882

[51] Int. Cl.[7] .............. A61K 31/34; A61K 31/38; A61K 31/445; C07D 307/79; C07D 333/54

[52] U.S. Cl. .............. 514/23.5; 514/255; 514/315; 514/422; 514/432; 514/456; 514/469; 536/29.2; 544/109; 544/374; 546/248; 548/525; 548/527; 549/23; 549/58; 549/406; 549/467

[58] Field of Search ................ 514/231.5, 255, 514/315, 422, 432, 443, 456, 469; 544/109, 374; 546/248; 548/525, 527; 549/23, 58, 406, 467; 536/29.2

[56] References Cited

U.S. PATENT DOCUMENTS 4,326,055 4/1982 Loeliger.

FOREIGN PATENT DOCUMENTS

| 0 568 898 | of 0000 | European Pat. Off. |
| 0 790 228 A1 | 8/1997 | European Pat. Off. |
| 96 13478 | of 0000 | WIPO. |
| 97 29100 | of 0000 | WIPO. |

Primary Examiner—Johann Richter
Assistant Examiner—Taofiq A. Solola
Attorney, Agent, or Firm—Burns, Doane, Swecker & Mathis, L.L.P.

[57] ABSTRACT

The present invention provides novel heteroaryl compounds having the general formula (I):

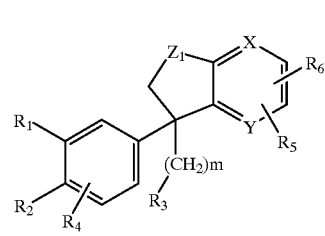

their pharmaceutical compositions to be used as human and veterinary medicine, particularly in the treatment of dermatological, rheumatic, respiratory, cardiovascular and ophthalmologic conditions, and their use in cosmetic compositions.

21 Claims, 1 Drawing Sheet

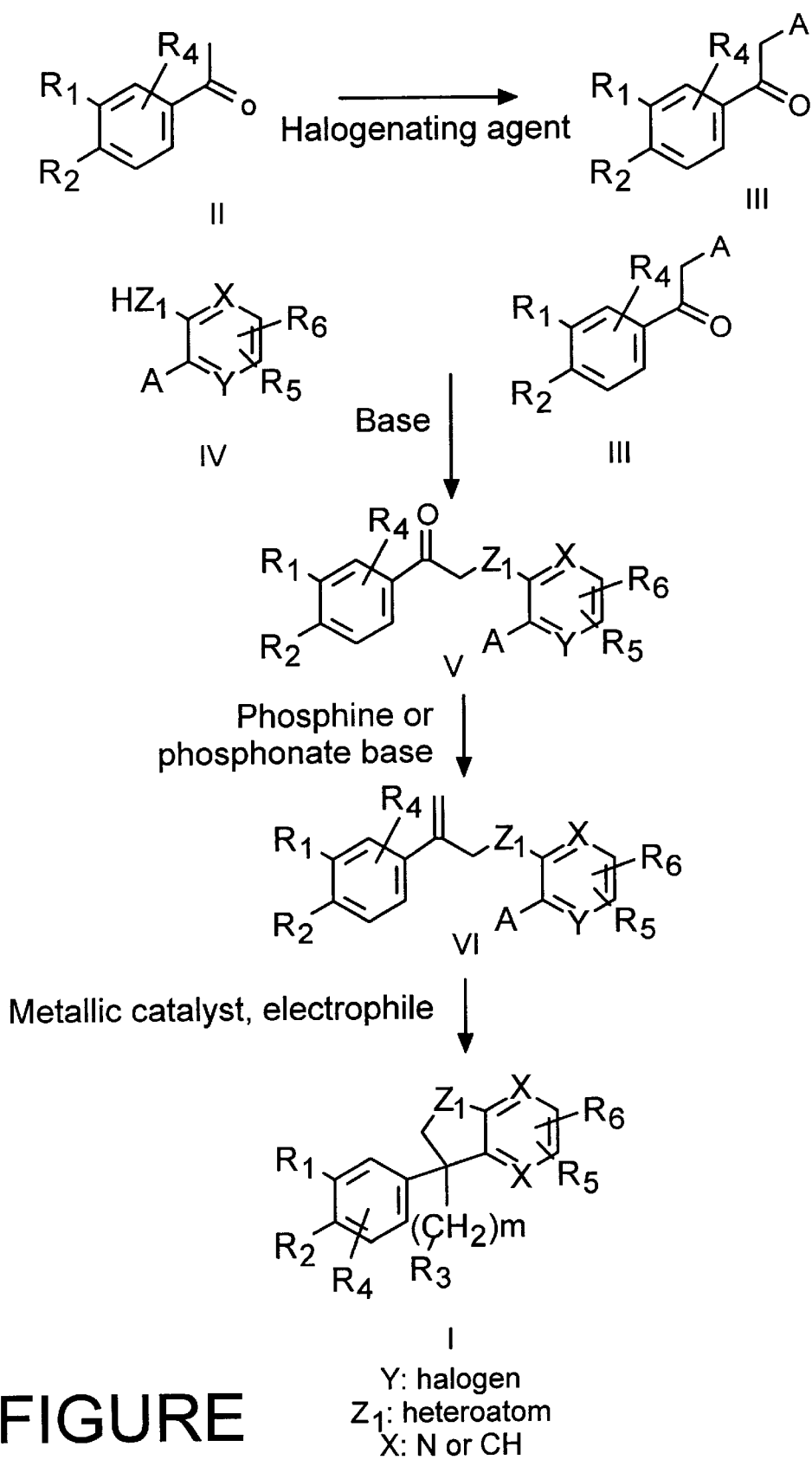
FIGURE

BENZOFURAN-ACRYLIC ACID DERIVATIVES AND THEIR USE AS MODULATORS OF RXRS OR RARS RECEPTORS

This application is a 371 of PCT/FR97/02205 filled Dec. 4, 1997.

FIELD OF THE INVENTION

The invention relates, by way of novel and useful industrial products, to biaromatic compounds. It likewise relates to the use of these novel compounds in pharmaceutical compositions intended for use in human or veterinary medicine, or alternatively in cosmetic compositions.

SUMMARY OF THE INVENTION

The compounds according to the invention have a marked activity in the fields of cell differentiation and proliferation, and find applications more particularly in the topical and systemic treatment of dermatological conditions connected with a keratinization disorder, dermatological conditions (or others) with an inflammatory and/or immunoallergic component, and dermal or epidermal oroliferations whether they are benign or malignant. These compounds can additionally be used in the treatment of degenerative diseases of the conjunctival tissue, for combating aging of the skin, whether it is photoinduced or chronological, and treating cicatrization disorders. In addition, they are used in the ophthalmological field, especially in the treatment of corneopathies.

It is likewise possible to use the compounds according to the invention in cosmetic compositions for body and hair hygiene.

The present invention relates to compounds which can be represented by the following general formula (I):

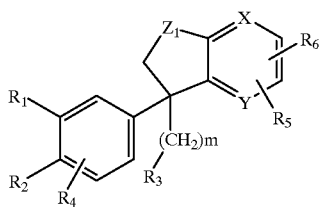

(I)

in which:

$Z_1$ is an atom or a radical chosen from amongst: O, S and NR',

X and Y, which are identical or different, are CH or N, it being understood that X and Y cannot simultaneously be nitrogen atoms, $R_1$ and $R_2$ taken together form, with the adjacent aromatic ring, a ring with 5 or 6 members which is optionally substituted by methyl groups and/or optionally interrupted by an SO radical, an $SO_2$ radical, or an oxygen or sulphur atom, $R_3$ is:
(i) a hydrogen atom, a lower alkyl radical, a lower alkenyl radical, a lower alkynyl radical, an aryl radical, a monohydroxyalkyl or polyhydroxyalkyl radical, a polyether radical, a cyano radical or an —O—$R_7$ radical, $R_7$ having the meaning given below, (ii) a radical of formula:

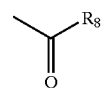

$R_8$ having the meaning given below, or (iii) a radical of formula:

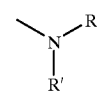

R and R' having the meaning given below $R_4$ is:
(i) a hydrogen atom,
(ii) a lower alkyl radical,
(iii) a halogen atom,
(iv) an —$OR_7$ , radical,
$R_7$ having the meaning given below, $R_5$ is:
(i) a radical of formula:

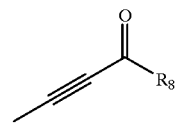

(ii) a radical of formula:

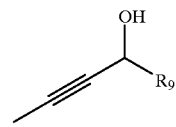

(iii) a radical of formula:

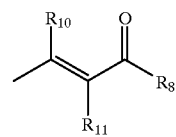

(iv) a radical of formula:

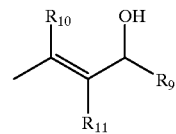

(v) a radical of formula:

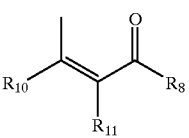

(vi) a radical of formula:

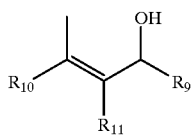

$R_8$, $R_9$, $R_{10}$ and $R_{11}$ having the meanings given below,
$R_6$ is a hydrogen atom, a halogen atom, a lower alkyl radical or the —$OR_7$ radical,
$R_7$ having the meaning given below,
$R_7$, which is identical or different, is a hydrogen atom, a lower alkyl radical, an aryl radical, an aralkyl radical, which is optionally substituted, a monohydroxyalkyl or polyhydroxyalkyl radical, a polyether radical or a lower acyl radical, $R_8$, which is identical or different, is:

(a) a hydrogen atom, a lower alkyl radical,
(b) a radical of formula:

R and R' having the meaning given below,
(c) an —$OR_{12}$ radical
(d) a sugar or amino acid residue,
$R_9$, which is identical or different, is a hydrogen atom or a lower alkyl radical,
$R_{10}$ and $R_{11}$, which are identical or different, are a hydrogen atom or a lower alkyl radical,
$R_{12}$ is a hydrogen atom, a lower alkyl radical, a mono- or polyhydroxyalkyl radical, an optionally substituted aryl or aralkyl radical,
R and R', which are identical or different, are protecting groups of amine functions, a hydrogen atom, a lower alkyl radical or alternatively, taken together, form a heterocycle,
m is equal to 0 or 1,
and the optical isomers of the said compounds of formula (I) as well as their salts.

When the compounds according to the invention are present in the form of salts, by addition of an acid, they are pharmaceutically or cosmetically acceptable salts obtained by addition of a mineral or organic acid, in particular hydrochloric, sulphuric, acetic, citric, fumaric, hemisuccinic, maleic and mandelic acid. When the compounds according to the invention are present in the form of salts by addition of a base, they are preferentially salts of an alkali or alkaline earth metal or alternatively of zinc or of an organic amine.

Preferred lower alkyl radicals are a radical having 1 to 6 linear or branched carbon atoms, optionally substituted by one or more halogen atoms. It is more particularly possible to mention the methyl, ethyl, isopropyl, butyl, tertiary butyl and hexyl radicals.

Preferred lower alkenyl radicals are a radical having from 2 to 6 linear or branched carbon atoms containing one or more double bonds and preferably allyl or vinyl radicals.

Lower alkynyl radicals are understood as meaning a radical having from 3 to 6 linear or branched carbon atoms containing one to several triple bonds. It is more particularly possible to mention the propargyl radical.

Lower acyl radical is understood as meaning a radical having from 1 to 6 carbon atoms and, preferably, the acetyl, propionyl or pivaloyl radicals.

Protective group of amine function is understood as meaning the corresponding groups described in "Protecting groups in organic synthesis" by T. W. Greene, Ed. by John Wiley and Sons (1981).

Polyether radical is understood as meaning a radical having 1 to 6 carbon atoms and 1 to 3 oxygen or sulphur atoms, such as the methoxymethyl ether, methoxyethoxymethyl ether or methylthiomethyl ether radicals.

Monohydroxyalkyl or polyhydroxyalkyl radical must be understood as a radical containing 1 to 6 carbon atoms and 1 to 5 hydroxyl groups.

Preferred polyhydroxyalkyl radicals are a radical having 3 to 6 carbon atoms and 2 to 5 hydroxyl groups, such as the 2,3-dihydroxypropyl, 2,3,4-trihydroxybutyl, 2,3,4,5-tetrahydroxypentyl radicals or the pentaerythritol residue.

Preferred optionally substituted aryl radicals are a phenyl radical, optionally substituted by one or more halogen atoms, a hydroxyl function or nitro function, a methoxy group or an optionally substituted amine function.

Preferred optionally substituted aralkyl radicals are the benzyl or phenethyl radical, optionally substituted by one or more halogen atoms, a hydroxyl or nitro function, or a methoxy group.

Preferred amino acid residues are a residue derived, for example, from at least one of the 20 constitutive amino acids of L or D configuration of mammalian proteins. They are more particularly chosen from amongst the residues derived from lysine, glycine or aspartic acid.

Preferred sugar residues are a residue derived, for example, from glucose, galactose, mannose or glucuronic acid.

Preferred heterocycles are a piperidino, morpholino, pyrrolidino or piperazino radical, optionally substituted in position 4 by a $C_1$–$C_6$ alkyl radical or by a mono- or polyhydroxyalkyl such as defined above.

When the $R_4$ and $R_6$ radicals are a halogen atom, this is preferably a fluorine, bromine or chlorine atom. It is the same for the radicals defined above which are substituted by a halogen atom or atoms.

Among the compounds of formula (I) above coming within the scope of the present invention, it is especially possible to mention the following:
ethyl 3-[3-(5,5,7,8-tetrahydro-5,5,8,8-tetramethyl-2-naphthyl)-3-methyl-2,3-dihydrobenzofuran-5-yl]-acrylate,
3-[3-(5,6,7,8-tetrahydro-5,5,8,8-tetramethyl-2-naphthyl)-3-methyl-2,3-dihydrobenzofuran-5-yl]acrylic acid,
[3-methyl-3-(5,5,8,8-tetramethyl-5,6,7,8-tetrahydronaphthalen-2-yl)-2,3-dihydrobenzofuran-5-yl] propynoic acid.
ethyl (+)-3-[3-methyl-3-(5,5,8,8-tetramethyl-5,6,7,8-tetrahydronaphthalen-2-yl)-2,3-dihydrobenzofuran-5-yl]-acrylate
(+)-3-[3-methyl-3-(5,5,8,8-tetramethyl-5,6,7,8-tetrahydronaphthalen-2-yl)-2,3-dihydrobenzofuran-5-yl]-acrylic acid
ethyl (−)-3-[3-methyl-3-(5,5,8,8-tetramethyl-5,6,7,8-tetrahydronaphthalen-2-yl)-2,3-dihydrobenzofuran-5-yl]-acrylate
(−)-3-[3-Methyl-3-(5,5,8,8-tetramethyl-5,6,7,8-tetrahydronaphthalen-2-yl)-2,3-dihydrobenzofuran-5-yl]-acrylic acid.
ethyl 3-[3-methyl-3-(3,5,5,8,8-pentamethyl-5,6,7,8-tetrahydronaphthalen-2-yl)-2,3-dihydrobenzofuran-5-yl]-acrylate
3-[3-methyl-3-(3,5,5,8,8-pentamethyl-5,6,7,8-tetrahydronaphthalen-2-yl)-2,3-dihydrobenzofuran-5-yl]-acrylic acid.

ethyl 3-[3-methyl-3-(naphthalen-2-yl)-2,3-dihydrobenzofuran-5-yl]acrylate

3-[3-methyl-3-(naphthalen-2-yl)-2,3-dihydrobenzofuran-5-yl]acrylic acid.

ethyl 3-[3-(8,8-dimethyl-5,6,7,8-tetrahydronaphthalen-2-yl)-3-methyl-2,3-dihydrobenzofuran-5-yl]acrylate 3-[3-(8,8-dimethyl-5,6,7,8-tetrahydronaphthalen-2-yl)-3-methyl-2,3-dihydrobenzofuran-5-yl]acrylic acid ethyl 3-[3-(5,5-dimethyl-5,6,7,8-tetrahydronaphthalen-2-yl)-3-methyl-2,3-dihydrobenzofuran-5-yl]acrylate.

3-[3-(5,5-dimethyl-5,6,7,8-tetrahydronaphthalen-2-yl)-3-methyl-2,3-dihydrobenzofuran-5-yl]acrylic acid.

ethyl 3-[3-methyl-3-(5,5,8,8-tetramethyl-5,6,7,8-tetrahydronaphthalen-2-yl)-2,3-dihydrobenzofuran-6-yl]-acrylate.

3-[3-methyl-3-(5,5,8,8-tetramethyl-5,6,7,8-tetrahydronaphthalen-2-yl)-2,3-dihydrobenzofuran-6-yl] acrylic acid.

ethyl 3-[3-allyl-3-(5,5,8,8-tetramethyl-5,6,7,8-tetrahydronaphthalen-2-yl)-2,3-dihydrobenzofuran-5-yl]-acrylate 3-[3-allyl-3-(5,5,8,8-tetramethyl-5,6,7,8-tetrahydronaphthalen-2-yl)-2,3-dihydrobenzofuran-5-yl] acrylic acid methyl (E)-3-[3-methyl-3-(5,5,8,8-tetramethyl-5,6,7,8-tetrahydronaphthalen-2-yl)-2,3-dihydrobenzofuran-5-yl]-but -2-enaote methyl (Z)-3-[3-methyl-3-(5,5,8,8-tetramethyl-5,6,7,8-tetrahydronaphthalen-2-yl)-2,3-dihydrobenzofuran-5-yl]-but-2-enoate.

(E)-3-[3-methyl-3-(5,5,8,8-tetramethyl-5,6,7,8-tetrahydronaphthalen-2-yl)-2,3-dihydrobenzofuran-5-yl] but-2-enoic acid ethyl 3-[3-methyl-3-(5,5,8,8-tetramethyl-5,6,7,8-tetrahydronaphthalen-2-yl)-2,3-dihydrobenzo[b]thiophen-5-yl]acrylate.

3-[3-methyl-3-(5,5,8,8-tetramethyl-5,6,7,8-tetrahydronaphthalen-2-yl)-2,3-dihydrobenzo[b]thiophen-5-yl]-acrylic acid.

ethyl 3-[3-(5,6,7,8-tetrahydro-5,5,8,8-tetramethyl-2-naphthyl)-7-methoxy-3-methyl-2,3-dihydrobenzofuran-5-yl]acrylate 3-[3-(5,6,7,8-tetrahydro-5,5,8,8-tetramethyl-2-naphthyl)-7-methoxy-3-methyl-2,3-dihydrobenzofuran-5-yl]acrylic acid.

N-(4-hydroxyphenyl)-3-[7-methoxy-3-methyl-3-(5,5,8,8-tetramethyl-5,6,7,8-tetrahydronaphthalen-2-yl)-2,3-dihydrobenzofuran-5-yl]acrylamide.

3-[3-methyl-3-(5,5,8,8-tetramethyl-5,6,7,8-tetramethyl-5,6,7,8-tetrahydronaphthalen-2-yl)-2,3-dihydro-1H-indol-5-yl] acrylic acid.

methyl 3-[3-methyl-3-(5,5,8,8-tetramethyl-5,6,7,8-tetrahydronaphthalen-2-yl]-2,3-dihydro-1H-indol-5-yl] acrylate.

BRIEF DESCRIPTION OF THE FIGURE

FIG. 1 is a reaction scheme for the preparation of the compounds of formula (I).

DETAILED DESCRIPTION OF THE PREFERRED EMBODIMENT

According to the present invention, the more particularly preferred compounds of formula (I) are those for which at least one, and preferably all, of the conditions below are respected:

$R_1$ and $R_2$, taken together, form an aromatic ring such as described above, $R_3$ is a hydrogen, a lower alkenyl radical, a no lower alkyl radical or an —$OR_7$ radical $R_4$ is a hydrogen, $R_5$ is a radical of formula (i) or (iii), $R_6$ is a hydrogen, $R_8$ is an $OR_{12}$ radical, X and Y are CH, $Z_1$ is an oxygen or sulphur atom.

An object of the present invention is likewise processes for preparation of the compounds of formula (I), in particular according to the reaction schemes given in FIG. 1.

Thus the compounds of general formula (I) can be obtained (FIG. 1) starting from the ketone (II), by halogenation, for example by means of a brominating agent such as bromine. The compound (III) obtained is then coupled to the compound (IV), in the presence of a base such as potassium carbonate or sodium hydride. The coupled derivative (V) is subjected to the action of a phosphine or of a phosphonate in the presence of a base leading to the compound (VI). The compound (VI) is cyclized by the action of a metallic catalyst such as palladium diacetate, in the presence of a hydride donor such as formic acid or of a nucleophile such as vinyltributyltin or lithium acetate and if necessary of a base. The addition of salts or of silver zeolites such as $Ag_3PO_4$ and of chiral phosphines such as Binap allows only one of the enantiomers to be obtained.

The products of general formula (I) thus obtained can serve as starting products for the production of other compounds of general formula (I). These products are obtained according to the classical synthesis methods employed in chemistry, such as those described in "Advanced Organic Chemistry" by J. March; John Willey and Sons, 1985.

For example, it is possible to carry out the functional modifications on the $R_5$ group as indicated below:

| | |
|---|---|
| carboxylic acid | → ester |
| ester | → carboxylic acid |
| acid | → acid chloride |
| acid chloride | → amide |
| acid | → amide |
| acid | → alcohol |
| alcohol | → aldehyde |
| amide | → amine |
| thiol | → thioether |
| thioether | → sulphoxide |
| thioether | → sulphone |
| sulphonic acid | → sulphonic ester |
| sulphonic acid | → sulphonamide |
| sulphinic acid | → sulphinic ester |

When $R_3$ is the —COON: radical, the compounds are preferentially prepared by protecting $R_3$ by a protecting group of allyl, benzyl or tert-butyl type.

The conversion to the free form can be accomplished:

in the case of an allyl protecting group, by means of a catalyst such as certain transition metal complexes in the presence of a secondary amine.

in the case of a benzyl protecting group, by debenzylation in the presence of hydrogen, by means of a catalyst such as palladium on carbon.

in the case of a tert-butyl protecting group by means of trimethylsilyl iodide.

When $R_5$ is an alcohol function the compounds can be obtained starting from corresponding aldehyde derivatives by action of an alkali metal hydride, such as sodium borohydride, in an alcoholic solvent (for example methanol), or by coupling of the corresponding halogenated derivative to a derivative of 3-(tributyltin)allyl alcohol.

When $R_5$ is an aldehyde function, the compounds can be obtained starting from alcohol derivatives by oxidation in the presence of manganese oxide, pyridinium dichromate or Swern's reagent.

When $R_5$ is an amide function the compounds can be obtained starting from corresponding carboxylic derivatives by reaction with aliphatic, aromatic or heterocyclic amines either by the intermediary of an acid chloride or in the presence of dicyclohexylcarbodiimide or of carbonyldiimidazole.

Certain of these compounds are bound to RXR receptors, some having an agonist activity, others an antagonist activity.

The binding and transactivation properties as agonist to the RXR receptors are determined by methods known in the art, such as, for example: MARTIN, B. et al., Skin Pharmacol., 1992, 5, 57–65; CAVEY, M. T. et al., Anal. Biochem., 1990, 186, 19–23; LEVER et al., Nature 1992, 355, 359–61; ALLENBY et al., Proc. Natl. Acad. Scd., 1993, 90, 30–4; ALLENBY et al., J. Biol. Chem., 1994, 269, 16689–95.

The RXR agonist activity is also determined by the test such as is described in the French Patent Application No. 95-07301 filed on Jun. 19, 1995 by the Applicant. This test comprises the following steps: (i) a sufficient quantity of a compound which is an active ligand of at least one receptor of the steroid/thyroid nuclear receptor superfamily other than a specific ligand of the RXR receptors and able to heterodimerize with the RXRs such as an agonist molecule of the RARs is applied topically to one part of the skin of a mammal, (ii) a molecule capable of having an agonist activity on the RXRs is administered by the systemic or topical route to this same part of the skin of the mammal before, during or after step (i), (iii) the response on the part of the mammal skin treated in this way is evaluated. Thus the response to a topical application on the ear of a mammal of an RAR agonist molecule which corresponds to an increase in the thickness of this ear can be increased by the administration by the systemic or topical route of an RXR receptor agonist molecule.

The RXRα antagonist activity is evaluated in the transactivation test by determination of the dose ($IC_{50}$) which inhibits the transactivator activity of a selective RXRα agonist by 50%: 6-(3,5,5,8,8-pentamethyl- 5,6,7,8-tetrahydro-2-naphthylthio)nicotinic acid (CD 2809) according to the following protocol:

The Hela cells are co-transfected with an expression vector coding for RXRα (p565-RXRα) and a reporter plasmid containing the response element ½ CRBP II cloned upstream of the thymidine kinase heterologous promoter and of the chloramphenicolm acetyl transferase (CAT) reporter gene. Eighteen hours after co-transfection the cells are treated with a fixed concentration of CD 2809 and increasing concentrations of the molecule to be evaluated. After twenty four hours' treatment, the determination of the CAT activity is carried out by ELISA. The fixed concentration of CD2809 used is $5 \cdot 10^{-8}M$ and corresponds to its $EC_{50}$.

Certain of the compounds according to the invention are bound to the RAR receptors and have an activity in the mouse embryonic teratocarcinoma cell (F9) differentiation test (Cancer Research 43, p. 5268, 1983) and/or in the ornithine decarboxylase inhibition test after induction by TPA in the mouse (Cancer research 38, p. 793–801, 1978). These tests show the activities of these compounds respectively in the fields of differentiation and of cell proliferation.

An object of the present invention is thus the compounds of formula (I) such as defined above by way of medicament.

The compounds according Lo the invention are particularly well-suited in the following fields of treatment:

1) to treat dermatological conditions connected with a keratinization disorder bearing on differentiation and on proliferation, especially to treat acne vulgaris, comedonian acne, polymorphic acne, acne rosacea, nodulocystic acne, acne conglobata, senile acne, secondary acne such as solar acne, acne medicamentosa or occupational acne, 2) to treat other types of keratinization disorders, especially ichthyosis, ichthyosiform states, Darrier's disease, keratosis palmaris and plantaris, leucoplakias and leucoplakiform states, cutaneous or mucous (buccal) lichen, 3) to treat other dermatological conditions connected with a keratinization disorder with an inflammatory and/or immunoallergic component and especially all the forms of psoriasis whether it is cutaneous, mucous or ungual, and even arthropathic psoriasis, or alternatively cutaneous atopy, such as eczema or respiratory atopy or alternatively gingival hypertrophy; the compounds can likewise be used in certain inflammatory conditions not presenting a keratinization disorder, 4) to treat all the dermal or epidermal proliferations whether they are benign or malignant, whether or not they are of a viral origin such as verruca vulgaris, verruca plana and epidermodysplasia verruciformis, oral or florid papillomatosis and proliferations able to be induced by ultra-violet, especially in the case of basal and spinocellular epithelioma, 5) to treat other dermatological disorders such as bullosis and collagen diseases, 6) to treat certain ophthalmological disorders, especially corneopathies, 7) to repair or combat aging of the skin, whether it is photoinduced or chronological, or to reduce pigmentation and actinic keratosis, or any pathologies associated with chronological or actinic aging, 8) to prevent or cure the stigmata of epidermal and/or dermal atrophy induced by local or systemic corticosteroids, or any other form of cutaneous atrophy, 9) to prevent or treat cicatrization disorders, to prevent or to repair vibices, or alternatively to promote cicatrization, 10) to combat sebaceous function disorders such as hyperseborrhoea of acne or simple seborrhoea, 11) in the treatment or the prevention of cancerous or precancerous states, 12) in the treatment of inflammatory disorders such as arthritis, 13) in the treatment of any disorder of viral origin at the cutaneous or general level, 14) in the prevention or the treatment of alopecia, 15) in the treatment of dermatological or general disorders with an immunological component, 16) in the treatment of disorders of the cardiovascular system such as arteriosclerosis, 17) in the treatment of cutaneous disorders due to exposure to U.V. rays.

In the therapeutic fields mentioned above, the compounds according to the invention can be advantageously employed in combination with other compounds of retinoid type activity, with D vitamins or their derivatives, with corticosteroids, with anti-free radicals, α-hydroxy or α-keto acids or their derivatives, or in addition alternatively with ion channel blockers. D vitamins or their derivatives are understood, for example, as meaning the derivatives of vitamin $D_2$ or $D_3$ and in particular 1,25-dihydroxy vitamin $D_3$. Anti-free radicals are understood, for example, as meaning α-tocopherol, Super Oxide Dismutase, Ubiquinol or certain metal chelators. α-Hydroxy or α-keto acids or their derivatives are understood, for example, as meaning lactic, malic, citric, glycolic, mandelic, tartaric, glyceric or ascorbic acid or their salts, amides or esters. Finally, ion channel blockers are understood, for example, as meaning Minoxidil (2,4-diamino-6-piperidinopyrimidine-3-oxide) and its derivatives.

An object of the present invention is likewise medicament compositions comprising at least one compound of formula (I) such as defined above, one of its optical or geometric isomers or one of its salts.

An object of the present invention is thus a novel medicament composition intended especially for the treatment of the abovementioned conditions, and which is characterized by the fact that it comprises, in a support which is pharmaceutically acceptable and compatible with the method of administration reserved for the latter, at least one compound of formula (I), one of its optical or geometric isomers or one of its salts.

The administration of the compounds according to the invention can be carried out by the enteral, parenteral, topical or ocular route.

By the enteral route, the medicaments can be present in the form of tablets, gelatin capsules, coated tablets, syrups, suspensions, solutions, powders, granules, emulsions, microspheres or nanospheres or lipid or polymer vesicles allowing controlled liberation. By the parenteral route, the compositions can be present in the form of solutions or suspensions for perfusion or for injection.

The compounds according to the invention are generally administered in a daily dose of approximately 0.01 mg/kg to 100 mg/Kg of body weight, and the latter at the rate of 1 to 3 administrations.

By the topical route, the base pharmaceutical compositions of compounds according to the invention are more particularly intended for the treatment of the skin and of the mucous membranes and can then be present in the form of ointments, creams, milks, lotions, powders, impregnated pads, solutions, gels, sprays, lotions or suspensions. They can likewise be present in the form of microspheres or nanospheres or lipid or polymer vesicles or polymer patches and hydrogels allowing controlled liberation.

These compositions by the topical route can in addition be present either in anhydrous form, or in an aqueous form, according to the clinical indication.

By the ocular route, these are principally collyriums.

These compositions for topical or ocular use contain at least one compound of formula (I) such as defined above, or one of its optical or geometric isomers or additionally one of its salts, at a preferred concentration of between 0.001% and 5% by weight with respect to the total weight of the composition.

The compounds of formula (I) according to the invention likewise have an application in the cosmetic field, in particular in body and hair hygiene and especially for the treatment of skins prone to acne, for the regrowth of the hair, prevention of hair loss, for combating a greasy appearance of the skin or of the hair, in protection against harmful aspects of the sun or in the treatment of physiologically dry skins, to prevent and/or to combat photoinduced or chronological aging.

In the cosmetic field, the compounds according to the invention can additionally be advantageously employed in combination with other compounds of retinoid type activity, with the D vitamins or their derivatives, with corticosteroids, with anti-free radicals, α-hydroxy or α-keto acids or their derivatives, or alternatively with ion channel blockers, all these different products being such as defined above.

The present invention is thus likewise directed at a cosmetic composition which is characterized by the fact that it comprises, in a support which is cosmetically acceptable and suitable for topical application, at least one compound of to formula (I) such as defined above or one of its optical or geometric isomers or one of its salts, this cosmetic composition especially being able to be present in the form of a cream, a milk, a lotion, a gel, microspheres or nanospheres or lipid or polymer vesicles, a soap or a shampoo.

The concentration of compound of formula (I) in the cosmetic compositions according to the invention is advantageously between 0.001% and 3% by weight with respect to the whole of the composition.

The medicament and cosmetic compositions according to the invention can additionally contain inert or even pharmacodynamically or cosmetically active additives or combinations of these additives, and especially: wetting agents; depigmenting agents such as hydroquinone, azelaic acid, caffeic acid or kojic acid; emollients; hydrating agents such as glycerol, PEG 400, thiamorpholinone, and its derivatives or alternatively urea; antiseborrhoeic or antiacne agents, such as S-carboxymethylcysteine, S-benzylcysteamine, their salts and their derivatives, or benzoyl peroxide; antibiotics such as erythromycin and its esters, neomycin, clindamycin and its esters, tetracyclines; antifungal agents such as ketoconazole or 4,5-polymethylene-3-isothiazolidones; agents promoting the regrowth of the hair, such as Minoxidil (2,4-diamino-6-piperidinopyrimidine-3-oxide) and its derivatives, Diazoxide (7-chloro-3-methyl-1,2,4-benzothiadiazine-1,1-dioxide) and Phenytoin (5,5-diphenylimidazolidine-2,4-dione); non-steroidal anti-inflammatory agents; carotenoids and, especially, β-carotene; anti-psoriatic agents such as anthralin and its derivatives; and finally eicosa-5,8,11,14-tetraynoic and eicosa-5,8,11-trynoic acids, their esters and amides.

The compositions according to the invention can likewise contain flavour-improving agents, preservatives such as the esters of parahydroxybenzoic acid, stabilizers, moisture regulators, pH regulators, osmotic pressure modifying agents, emulsifiers, UV-A and UV-B filters, antioxidants, such as α-tocopherol, butylhydroxyanisole or butylhydroxytoluene.

There will now be given, by way of illustration and without any limiting character, several examples of obtainment of active compounds of formula (I) according to the invention, as well as various actual formulations based on such compounds.

A. EXAMPLES OF COMPOUNDS

Example 1 ethyl 3-[3-(5,6,7,8-tetrahydro-5,5,8,8-tetramethyl-2-naphthyl)-3-methyl-2,3-dihydrobenzofuran-5-yl]-acrylate.

(a) 3-iodo-4-hydroxybenzoic acid.

A 3.6% solution of sodium perchlorate is added dropwise to a mixture of 4-hydroxybenzoic acid (1,2.75 g, 0.92 mol), sodium (3.7 g, 0.92 mol), sodium iodide (13.85 g, 0.92 mol) in methanol (350 ml) at 0° C. The mixture is stirred for two hours at 0° C. 100 ml of a solution of 10% sodium thiosulphate are added. After stirring, the mixture is acidified to pH 1 with hydrochloric acid. It is extracted with 600 ml of ethyl ether. The organic phase is washed twice with 400 ml of water, dried over magnesium sulphate and concentrated in vacuo at 40° C. in a rotary evaporator.

White solid. Mass: 28.76 g. Yield: 100%. M.p.: 157° C.

$^1$H [lacuna] NMR (DMSO, 250 MHz): 6.74 (1H Ar, d, J=8.4 Hz), 7.71 (1H Ar, d, J=8.4 Hz), 8.13 (1H Ar, s), 10.16 (1H, s), 11.12 (1H, s).

(b) methyl 3-iodo-4-hydroxybenzoate.

A solution of 3-iodo-4-hydroxybenzoic acid (28.76 g, 0.11 mol) and sulphuric acid (6.6 ml) in methanol (160 ml) is heated to reflux for 6 h. 300 ml of water are added and the mixture is alkalized to neutrality with sodium bicarbonate. It is extracted with ethyl ether (600 ml). The organic phase is washed twice with 400 ml of water, dried over magnesium sulphate and concentrated in vacuo at 40° C. in a rotary evaporator. The product is purified by flash chromatography on a silica column (ethyl acetate 10%, $CH_2Cl_2$ 90%)

White solid. Mass: 19.1 g. Yield: 63%. M.p.: 133° C.

(c) methyl 4-[(5,6,7,8-tetrahydro-5,5,8,8-tetramethyl-2-naphthoyl)methyloxy]-3-iodobenzoate.

A solution of 5,6,7,8-tetrahydro-5,5,8,8-tetramethyl-2-bromoacetonaphthone (9.8 g, 0.032 mol), methyl 4-hydroxy-3-iodobenzoate (8.8 g, 0.032 mol) and potassium carbonate (8.5 g, 0.062 mol) in methyl ethyl ketone (450 ml) is heated to reflux for 1 day. The reaction mixture is filtered, then concentrated in a rotary evaporator. 500 ml of water and 500 ml of ethyl ether are added. After stirring and separation, the organic phase is washed twice with 500 ml of water, dried over magnesium sulphate and concentrated in vacuo at 40° C. in a rotary evaporator. The product is purified by flash chromatography on a silica column (ethyl acetate 10%, heptane 90%).

White solid. Mass: 9.56 g. Yield: 60%. M.p.: 125° C.

$^1$H [lacuna] NMR ($CDCL_3$, 250 MHz): 1.30 (6H, s), 1.32 (6H, s), 1.71 (4H, s), 3.88 (3H, s), 5.40 (2H, s), 6.70 (1H Ar, d, J=8.7 Hz), 7.43 (1H Ar, d, J=8.5 Hz), 7.74 (1H Ar, dd, J=2 Hz, J=8.5 Hz), 7.93 (1H Ar, dd, J=8.7, J=2.3 Hz), 7.98 (1H Ar, d, J=2 Hz), 8.48 (1H Ar, d, J=2.3 Hz).

(d) methyl 3-iodo-4-[2-[5,6,7,8-tetrahydro-5,5,8,8-tetramethyl-2-naphthyl]-1-propenylloxy benzoate A 30% solution of sodium methoxide (2.67 g, 14.83 mmol) is added in 8 hours to a mixture of methyl 4-[5,6,7,8-tetrahydro-5,5,8,8-tetramethyl-2-naphthoyl)-methyloxy]-3-iodobenzoate (7.50 g, 14.8 mmol) and methyltryphenylphosphine bromide (7.30 g, 20.42 mmol) in THF (80 ml). The solution is stirred at ambient temperature for 18 h. The mixture is concentrated in vacuo at 40° C. in a rotary evaporator. It is extracted with 90 ml of ethyl ether and 90 ml of water. After separation, the organic phase is washed twice with 90 ml of water, dried over anhydrous magnesium sulphate and concentrated in vacuo at 40° C. in a rotary evaporator. The product is purified by flash chromatography on a silica column ($CH_2Cl_2$ 70%, heptane 30%).

White solid. Mass: 4.71 g. Yield: 63%. M.p.: 126° C.

$^1$H [lacuna] NMR ($CDCL_3$, 250 MHz): 1.29 (6H, s), 1.30 (6H, s), 1.69 (4H, s), 3.89 (3H, s), 4.99 (2H, s), 5.55 (1H, s), 5.59 (1H, s), 6.87 (1H Ar, d, J=8.7 Hz), 7.21 to 7.33 (2H Ar, m), 7.38 (1H Ar, d, J=1.8 Hz), 8.00 (1H Ar, dd, J=8.7, J=2 Hz), 8.48 (1H Ar, d, J=2 Hz)

$^{13}$C [lacuna] NMR ($CDCL_3$, 250 MHz): 31.79, 31.90, 34.16, 34.33, 34.96, 35.10, 52.09, 70.81, 85.85, 111.35, 112.73, 114.05, 123.33, 124.17, 124.46, 126.71, 129.67, 131.45, 131.74, 135.23, 141.06, 141.99, 145.05, 145.10, 160.67, 165.47.

(e) methyl 3-(5,6,7,8-tetrahydro-5,5,8,8-tetramethyl-2-naphthyl)-(3-methyl)-2,3-dihydrobenzofuran-5-carboxylate.

A mixture of tributhylamine (2.28 ml, 9.6 mmol), palladium diacetate (0.06 g, 0.3 mmol), formic acid (0.29 ml, 7.4 mmol) and methyl 3-Iodo-4-[2-[5,6,7,8-tetrahydro-5,5,8,8-tetramethyl-2-naphthyl]-1-propenylloxy benzoate (1.37 g, 2.72 mmol) in acetonitrile (25 ml) is heated at 95° C. for 4 h. The reaction mixture is concentrated in vacuo at 40° C. in a rotary evaporator. 40 ml of water and 40 ml of ethyl ether are added. After separation, the organic phase is washed twice with 20 ml of water, dried over magnesium sulphate, and concentrated in vacuo at 40° C. in a rotary evaporator. The product is purified by flash chromatography on a silica column ($CH_2Cl_2$ 50% heptane 50%)

White solid. Mass: 630 mg. Yield: 61%. M.p.: 74° C.

$^1$H [lacuna] NMR ($CDCL_3$, 250 MHz): 1.20 to 1.24 (12H, m), 1.65 (4H, s), 1.73 (3H, s), 3.83 (3H, s), 4.51 (1H, d, J=8.7 Hz), 4.66 (1H, d, J=8.7 Hz), 6.87 (1H Ar, d, J=8.3 Hz), 6.96 (1H Ar, dd, J=8.3, J=2 Hz), 7.19 to 7.24 (2H Ar, m), 7.73 (1H Ar, d, J=1.8 Hz), 7.92 (1H Ar, dd, J=8.3, J=2 Hz).

$^{13}$C [lacuna] NMR ($CDCL_3$, 250 MHz): 26.63, 31.99, 32.08, 32.11, 34.18, 35.21, 35.32, 49.45, 52.04, 87.37, 109.82, 123.31, 123.98, 124.36, 126.46, 126.85, 131.41, 136.62, 142.56, 143.49, 145.04, 163.91, 167.19.

(f) 3-(5,6,7,8-tetrahydro-5,5,8,8-tetramethyl-2-naphthyl)-3-methyl-2,3-dihydrobenzofuran-5-carboxylic acid A mixture of methyl 3-(5,6,7,8-tetrahydro-5,5,8,8-tetramethyl-2-naphthyl)-(3-methyl)-2,3-dihydrobenzofuran-5-carboxylate (510 mg, 135 mmol), sodium hydroxide (0.33 g, 7.9 mmol), and lithium hydroxide (0.33 g, 7.9 mmol) is stirred 5 days at ambient temperature. It is concentrated in vacuo at 40° C. in a rotary evaporator. 10 ml of water and 10 ml of ethyl acetate are added again. The mixture is acidified to pH 1 with a concentrated hydrochloric acid solution. After separation, the organic phase is washed twice with 10 ml of water, dried over magnesium sulphate, and concentrated in vacuo at 40° C. in a rotary evaporator. The solid obtained is washed with heptane.

White solid. Mass: 400 mg. Yield: 83%. M.p.: 246° C.

$^1$H [lacuna] NMR (DMSO, 250 MHz): 1.20 to 1.23 (12H, m), 1.64 (4H, s), 1.74 (3H, s), 3.83 (3H, s), 4.44 (1H, d, J=8.7 Hz), 4.66 (1H, d, J=8.7 Hz), 6.85 (1H Ar, d, J=7.5 Hz), 6.96 (1H Ar, dd, J=8.3, J=2 Hz), 7.19 to 7.24 (2H Ar, m), 7.73 (1H Ar, d, J=1.8 Hz), 7.92 (1H Ar, dd, J=8.3, J=2 Hz).

$^{13}$C [lacuna] NMR (DMSO, 250 MHz): 26.26, 31.63, 31.72, 31.75, 33.83, 34.25, 34.96, 35.06, 49.14, 87.01, 109.34, 123.36, 123.74, 124.03, 126.41, 126.52, 131.38, 136.25, 142.39, 143.02, 144.60, 163.59, 167.90.

(g) 3-(5,6,7,8-tetrahydro-5,5,8,8-tetramethyl-2-naphthyl)-3-methyl-2,3-dihydrobenzofuran-5-methanol 7.7 ml of a 1M solution of borane in THF are added dropwise at 0° C. to a solution of 3-(5,6,7,8-tetrahydro-5,5,8,8-tetramethyl-2-naphthyl)-3-methyl-2,3-dihydrobenzofuran-5-carboxylic acid (1.7 g, 4.7 mol) in THF (10 ml). The mixture is stirred for 4 hours at ambient temperature and then 2 ml of a solution of THF and water (1:1) are added. After concentration in vacuo at 40° C. in a rotary evaporator. The mixture is extracted with ethyl acetate. The organic phase is washed with water, dried over anhydrous magnesium sulphate, concentrated in vacuo at 40° C. in a rotary evaporator. The product is purified by flash chromatography on a silica column.

Yellow amorphous [lacuna]. Mass: 1.7 g. Yield: 100%. NMR δ ppm:

$^1$H [lacuna] ($CDCl_3$): 1.20 to 1.25 (12H, m) 1.66 (4H, s), 1.72 (3H, s), 3.47 (1H, s), 4.44 (1H, d, J=8.8 Hz), 4.59 (2H, s), 4.60 (1H, d, J=8.8 Hz), 6.84 (1H Ar, d, J=8 Hz), 7.01 (1H Ar, dd, J=8.3, J=2.3 Hz), 7.05 (1H Ar, d, J=1.8 Hz), 7.17 to 7.22 (3H Ar, m).

$^{13}$C [lacuna] (CDCl$_3$): 25.86, 31.39, 31.48, 31.51, 33.55, 33.97, 34.65, 34.75, 49.25, 65.05, 86.02, 109.29, 123.07, 123.45, 123.78, 126.11, 127.26, 133.18, 135.93, 142.38, 142.65, 144.27, 159.00.

(h) 3-(5,6,7,8-tetrahydro-5,5,8,8-tetramethyl-2-naphthyl)-3-methyl-2,3-dihydrobenzofuran-5-carbaldehyde.

A mixture of alcohol obtained above (1 g, 2.86 mmol) pyridinium dichromate 2.15 g, 5.7 mmol) in dichloromethane is stirred at ambient temperature for 3 h. After filtration and concentration in vacuo at 40° C. in a rotary evaporator, the product is purified by flash chromatography on a silica column.

Oil. Mass: 0.98 g, Yield: 98%.

NMR δ ppm:

$^1$H [lacuna] (CDCl$_3$): 1.20 to 1.26 (12H, m), 1.67 (4H, s), 1.76 (3H, s), 4.57 (d, 1H, J=8.9), 4.73 (d, 1H, J=8.9), 6.96 (1H Ar, s), 7.00 (1H Ar, s), 7.20 to 7.25 (2H Ar, m), 7.59 (1H Ar, d, J=1.5 Hz), 7.74 (1H Ar, dd, J=8.3 Hz, J=1.8 Hz), 9.83 (1H, s).

$^{13}$C [lacuna] (CDCl$_3$): 26.44, 31.77, 31.87, 31.91, 33.99, 34.39, 34.98, 35.09, 49.04, 87.45, 110.26, 123.74, 124.12, 125.52, 126.75, 130.90, 132.95, 137.68, 141.99, 143.48, 144.94, 155.10, 190.67.

(i) ethyl 3-[3-(5,6,7,8-tetrahydro-5,5,8,8-tetramethyl-2-naphthyl)-3-methyl-2,3-dihydrobenzofuran-5-yl]-acrylate 80% sodium hydride in oil (41 mg, 1.38 mmol) is added to a mixture of aldehyde obtained above and triethylphosphonoacetate (0.27 ml, 1.38 mmol) in THF (10 ml). The mixture is stirred for 4 h at ambient temperature, extracted with ethyl acetate and washed with water. After drying the organic phase is concentrated in vacuo at 40° C. in a rotary evaporator, the product is purified by flash chromatography on a silica column.

Oil. Mass: 330 mg, Yield: 69%.

NMR δ ppm:

$^1$H [lacuna] (CDCl$_3$): 1.18 to 1.33 (15H, m), 1.67 (4H, s), 1.73 (3H, s), 4.22 (2H, q, J=7.1 Hz), 4.49 (1H, d, J=8.8 Hz), 4.63 (1H, d, J=8.8 Hz), 6.24 (1H, d, 15.8 Hz), 6.87 (1H Ar, d, J=8.5 Hz), 6.99 (1H Ar, dd, J=8.3 Hz, J=2.3 Hz), 7.21 to 7.24 (3H Ar, m), 7.36 (1H Ar, d, J=8.3 Hz), 7.62 (1H Ar, d, J=15.8 Hz).

$^{13}$C [lacuna] (CDCl$_3$): 14.36, 26.34, 31.79, 31.91, 33.99, 34.40, 35.03, 35.14, 49.47, 60.25, 86.93, 110.23, 115.24, 123.79, 124.21, 126.66, 127.83, 129.67, 137.10, 142.32, 143.32, 144.71, 144.86, 161.79, 167.38.

Example 2

3-[3-(5,6,7,8-Tetrahydro-5,5,8,8-tetramethyl-2-naphthyl)-3-methyl-2,3-dihydrobenzofuran-5-yl]acrylic acid (a) 3-[3-(5,6,7,8-tetrahydro-5,5,8,8-tetramethyl-2-naphthyl)-3-methyl-2,3-dihydrobenzofuran-5-yl]acrylic acid A mixture of methyl 3-[3-(5,6,7,8-tetrahydro-5,5,8,8-tetramethyl-2-naphthyl)-3-methyl-2,3-dihydrobenzofuran-5-yl]acrylate (330 mg, 0.79 mmol), a 2N methanolic sodium hydroxide solution (4 ml, 7.9 mmol) in THF (3 ml) is heated for 5 hours at 60° C. The mixture is acidified to pH 1 with a concentrated hydrochloric acid solution, extracted with ethyl acetate and washed with water. After drying the organic phase is concentrated in vacuo at 40° C. in a rotary evaporator, the product is purified by flash chromatography on a silica column.

Yellow solid. Mass: 45 mg, Yield: 58%. M.p. 160° C.

NMR δ ppm:

$^1$H [lacuna] (CDCl$_3$): 1.21 to 1.26 (12H, m), 1.67 (4H, s), 1.74 (3H, s), 4.50 (2H, q, J=7 Hz), 4.64 (1H, d, J=8.8 Hz), 4.63 (1H, d, J=8.8 Hz), 6.27 (1H, d, 15.8 Hz), 6.88 (1H Ar, d, J=8.5 Hz), 6.99 (1H Ar, d, J=8.3 Hz), 7.21 to 7.24 (3H Ar, m), 7.38 (1H Ar, d, J=8.3 Hz), 7.69 (1H Ar, d, J=15.8 Hz).

$^{13}$C [lacuna] (CDCl$_3$): 26.35, 31.78, 31.89, 33.96, 34.38, 35.02, 35.11, 49.43, 86.93, 110.27, 115.05, 123.74, 124.06, 124.16, 126.65, 127.68, 129.92, 137.11, 142.26, 143.31, 144.86, 146.24, 161.98, 172.16.

Example 3

[3-Methyl-3-(5,5,8,8-tetramethyl-5,6,7,8-tetrahydronaphthalen-2-yl)-2,3-dihydrobenzofuran-5-yl]propynoic acid.

a) 5-(2,2dibromrovinyl)-3-methyl-3-(5,5,8,8-tetramethyl-5,6,7,8-tetrahydronaphthalen-2-yl)-2,3-dihydrobenzofuran Tetrabromomethane (1.22 g, 3.67 mmol) is added to a mixture of triphenylphosphine (1.93 g, 7.35 mmol) in dichloromethane (10 ml) at 0° C. The mixture is stirred at ambient temperature for 1 h, then a solution of 3-(5,6,7,8-tetrahydro-5,5,8,8-tetramethyl-2-naphthyl)-3-methyl-2,3-dihydrobenzofuran-5-carbaldehyde (850 mg, 2.45 mmol) in dichloromethane (2 ml) is added at 0° C. The stirring is continued for 2 h at ambient temperature, then the suspension is concentrated in vacuo in a rotary evaporator. The product is purified by chromatography on a silica column.

Colourless oil. Mass: 860 mg, Yield: 7° C.

b) [3-Methyl-3-(5,5,8,8-tetramethyl-5,6,7,8-tetrahydronaphthalen-2-yl)-2,3-dihydrobenzofuran-5-yl]propynoic acid A 1.6 M butyllithium solution (2.35 ml, 3.55 mmol) is added to a solution of 5-(2,2-dibromovinyl)-3-Methyl-3-(5,5,8,8-tetramethyl-5,6,7,8-tetrahydronaphthalen-2-yl)-2,3-dihydrobenzofuran (860 mg, 1.71 mmol) in THF (20 ml) at −78° C. Stirring is continued for 1 h at −78° C. and then carbon dioxide is bubbled in for 15 min. The temperature is allowed to return to ambient temperature. The solution is treated with ethyl acetate and with a solution of ammonium chloride, the organic phase is washed twice with water, dried over magnesium sulphate, and concentrated in vacuo at 40° C. in a rotary evaporator. The solid obtained is recrystallized in a heptane/ethyl ether mixture.

White solid. Mass: 98 mg. M.p. =125° C.

$^1$H [lacuna] NMR (CDCL$_3$, 250 MHz): 1.22 to 1.25 (12H, d) 1.66 (4H, s), 1.71 (3H, s), 4.50 (1H, d, J=8.7 Hz), 4.67 (1H, d, J=8.7 Hz), 6.64 (1H Ar, d, J=8.5 Hz), 6.94 (1H Ar, dd), 7.13 to 7.24 (3H Ar, m), 7.45 (1H Ar, dd).

Example 4 ethyl (+)-3-[3-methyl-3-(5,5,8,8-tetramethyl-5,6,7,8-tetrahydronaphthalen-2-yl)-2,3-dihydrobenzofuran-5-yl]-acrylate a) methyl (+)-3-[3-methyl-3-(5,5,8,8-tetramethyl-5,6,7,8-tetrahydronaphthalen-2-yl)-2,3-dihydrobenzofuran-5-yl] carboxylate.

A mixture of calcium carbonate (100 mg, 1 mmol), palladium diacetate (10 mg, 0.05 mmol), sodium formate (68 mg, 1 mmol), methyl 3-Iodo-4-[2-[5,6,7,8-tetrahydro-5, 5,8,8-tetramethyl-2-naphthyl]-1-propenyloxy benzoate (250 mg, 05 mmol), (S)-(−)-2,2'-Bis(diphenylphosphino)-1,1'-binaphthyl (65 mg, 0.1 mmol), and silver zeolite (Aldrich 35,860-9) in acetonitrile (7 ml) is heated at 60° C. for 4 d. The reaction mixture is filtered on celite and concentrated in vacuo at 40° C. in a rotary evaporator. Water and ethyl ether are added. After separation, the organic phase is washed twice with water, dried over magnesium sulphate, and concentrated in vacuo at 40° C. in a rotary evaporator. The product is purified by flash chromatography on a silica column.

White solid. Mass: 75 mg, Yield: 40%. α$_d$[CHCl$_3$]: +116.

The remainder of the synthesis is identical to that of the racemic mixture (Example 1).

b) ethyl (+)-3-[3-methyl-3-(5,5,8,8-tetramethyl-5,6,7,8-tetrahydronaphthalen-2-yl)-2,3-dihydrobenzofuran-5-yl] acrylate α$_d$[CHCl$_3$]: +227.

Example 5

(+)-3-[3--Methyl-3-(5,5,5,8-tetramethyl-5,6,7,8-tetrahydronaphthalen-2-yl)-2,3-dihydrobenzofuran-5-yl] acrylic acid α$_d$[CHCl$_3$]: +290.

Example 6 ethyl (+)-3-[3-methyl-3-(5,5,8,8-tetramethyl-5,6,7,8-tetrahydronaphthalen-2-yl)-2,3-dihydrobenzofuran-5-yl] acrylate a) Methyl (−)-3-[3-methyl-3-(5,5,8,8-tetramethyl-5,6,7,8-tetrahydronaphthalen-2-yl)-2,3-dihydrobenzofuran-5-yl] carboxylate.

The operating procedure is the same as that followed in Example 4a employing (R)-(+)-2,2'-bis(diphenylphosphino)-1,1'-binaphthyl as palladium diacetate ligand.

α$_d$[CHCl$_3$]: −145.

The remainder of the synthesis is identical to that of the racemic mixture (Example 1).

b) ethyl (−)-3-[3-methyl-3-(5,5,8,8-tetramethyl-5,6,7,8-tetrahydronaphthalen-2-yl)-2,3-dihydrobenzofuran-5-yl] acrylate α$_d$[CHCl$_3$]: −238

Example 7

(−)-3-[3-Methyl-3-(5,5,8,8-tetramethyl-5,5,7,8-tetrahydronaphthalen-2-yl)-2,3-dihydrobenzofuran-5-yl] acrylic acid α$_d$[CHCl$_3$]: −306.

Example 8 ethyl 3-[3-methyl-3-(3,5,5,8,8-pentamethyl-5,6,7,8-tetrahydronaphthalen-2-yl)-2,3-dihydrobenzofuran-5-yl]-acrylate a) Methyl 3-iodo-4-[2-oxo-2-(3,5,5,8,8-pentamethyl-5,6,7,8-tetrahydronaphthalen-2-yl)ethoxy]-benzoate.

The experimental procedure is analogous to hat followed for example 1c applied to methyl 3-iodo-4-hydroxybenzoate and 5,6,7,8-tetrahydro-3,5,5,8,8-pentamethyl-2-bromoacetonaphthone.

White powder. Yield: 1.65 g (86%). M.p.=89° C.

$^1$H [lacuna] NMR (CDCl$_3$) d: 1.29 (6H, s), 1.31 (6H, s), 1.70 (4H, s), 2.49 (3H, s), 3.88 (3H, s), 5.30 (2H, s), 7.19 (1H Ar, s), 7.30 (1H Ar, s), 7.37 (1H Ar, d, J=8 Hz), 7. 63 (1H Ar, s), 7.87 (1H Ar, d, J=8 Hz)

b) Methyl 3-iodo-4-[2-(3,5,5,8,8-pentamethyl-5,6,7,8-tetrahydronaphthalen-2-yl)-allyloxy]benzoate.

The experimental procedure is analogous to that followed for Example 1d applied to methyl 3-Iodo-4-[2-oxo-2-(3,5,5,8,8-pentamethyl-5,6,7,8-tetrahydronapthalen-2-yl) ethoxy]benzoate.

Colourless oil. Mass: 3.2 g. Yield: 40%.

$^1$H [lacuna] NMR (CDCl$_3$) d: 1.26 (6H, s), 1.29 (6H, s) 1.67 (4H, s), 2.29 (3H, s), 3.89 (3H, s), 4.75 (2H, s), 5.23 (1H, d, J=1.6 Hz), 5.77 (1H, d, J=1.6 Hz), 6.79 (1H Ar, d, J=8.7 Hz), 7.09(1H Ar, s), 7.13 (1H Ar, s), 7.98 (1H Ar, dd, J=8.7 Hz, J=2.1 Hz), 8.47 (1H Ar, d, J=2 Hz).

c) methyl 3-(5,6,7,8-tetrahydro-3,5,5,8,8-pentamethyl-2-naphthyl)-3-methyl-2,3-dihydrobenzofuran-5-carboxylate.

The experimental procedure is analogous to that followed for Example 1e applied to methyl 3-Iodo-4-[2-(3,5,5,8,8-pentamethyl-5,6,7,8-tetrahydronaphthalen-2-yl)allyloxy]benzoate.

Colourless oil. Mass: 1 g. Yield: 42%.

$^1$H [lacuna] NMR (CDCl$_3$) d: 1.24 to 1.28 (12H, m), 1.67 (4H, s), 1.76 (3H, s), 1.92 (3H, s), 3.85 (3H, s), 4.52 (1H, d, J=9.1 Hz), 4.81 (1H, d, J=9.1 Hz), 6.85 (1H Ar, d, J=8.4 Hz), 7.01 (1H Ar, s), 7.32 (1H Ar, s), 7.65 (1H Ar, d, J=1.8 Hz), 7.92 (1H Ar, dd, J=8.4 Hz, J=1.8 Hz).

$^{13}$C [lacuna] NMR (CDCl$_3$) d: 21.15 (CH$_3$), 29.52 (CH$_3$) 31.61 (CH$_3$ TTNN), 31.71 (CH$_3$ TTNN), 31.88 (CCH$_3$ TTNN) 31.95 (CH$_3$ TTNN), 33.72 (C. TTNN), 34.07 (C TTNN), 35.14 (CH$_2$ TTNN), 35.22 (CH$_2$ TTNN), 49.28 (C), 51.82 (OCH$_3$) 85.32 (CH$_2$O), 109.30 (CH Ar), 122.78 (C Ar), 125.14 (CH Ar), 124.36 (CH Ar), 125.96 (CH Ar), 130.77 (CH Ar), 131.12 (CH Ar), 131.56 (C Ar), 133.53 (C Ar), 138.60 (C Ar), 141.86 (C Ar), 143.64 (C Ar), 163.67 (C—O Ar), 167.29 (COO).

d) 3-(5,6,7,8-tetrahydro-3,5,5,8,8-pentamethyl-2-naphthyl)-3-methyl-2,3-dihydrobenzofuran-5-carbaldehyde.

A 1M solution of diisobutylaluminium hydride in toluene (5.82 ml, 5.82 mmol) is added dropwise at 0° C. to a solution of methyl 3-(5,6,7,8-tetrahydro-3,5,5,8,8-pentamethyl-2-naphthyl)-3-methyl-2,3-dihydrobenzofuran-5-carboxylate (1 g, 2.55 mmol) in toluene (30 ml). The solution is stirred for 1 h at 0° C., then treated with a solution of double tartrate of sodium and potassium, filtered on celite and taken up again in a mixture of ethyl ether and water. The organic phase is washed with water, dried over magnesium sulphate and concentrated in vacuo at 40° C. in a rotary evaporator.

A mixture of alcohol obtained above (1 g, 2.55 mmol) pyridinium dichromate (2 g, 5.3 mmol) in dichloromethane is stirred at ambient temperature for 4 h. After filtration and concentration in vacuo at 40° C. in a rotary evaporator, the product is purified by flash chromatography on a silica column.

Oil. Mass: 470 mg, Yield: 51%.

$^1$H [lacuna] NMR (CDCl$_3$) d: 1.25 to 1.27 (12H, m), 1.67 (4H, s), 1.78 (3H, s), 1.91 (3H, s), 4.56 (1H, d, J=9.2 Hz), 4.85 (1H, d, J=9.2 Hz), 6.95 (1H Ar, d, J=8.2 Hz), 7.02 (1H Ar, s), 7.32 (1H Ar, s), 7.52 (1H Ar, d, J=1.7 Hz), 7.72 (1H Ar, dd, J=8.7 Hz, J=1.7 Hz), 9.82 (1H, s).

e) ethyl 3-[3-methyl-3-(3,5,5,8,8-pentamethyl-5,6,7,8-tetrahydronaphthalen-2-yl)-2,3-dihydrobenzofuran-5-yl] acrylate The experimental procedure is analogous to that followed for Example 1i applied to 3-(5,6,7,8-tetrahydro-3,5,5,8,8-pentamethyl-2-naphthyl)-3-methyl-2,3-dihydrobenzofuran-5-carbaldehyde.

Colourless oil. Mass: 320 mg. Yield: 79%.

$^1$H [lacuna] NMR (CDCl$_3$) d: 1.25 to 1.33 (15H, m), 1.68 (4H, s), 1.76 (3H, s), 1.94 (3H, s), 4.21 (2H, q, J=7.2 Hz), 4.49 (1H, d, J=9.1 Hz), 4.78 (1H, d, J=9.1 Hz), 6.23 (1H, d, J=16 Hz), 6.83 (1H Ar, d, J=8.3 Hz), 7.02 (1H Ar, s), 7.15 (1H Ar, s), 7.31 (1H Ar, d, J=1 .8 Hz), 7.34 (1H Ar, d, J=8.3 Hz), 7.61 (1H, d, J=16 Hz).

Example 9

3-[3-Methyl-3-(3,5,5,8,8-pentamethyl-5,6,7,8-tetrahydronaphthalen-2-yl)-2,3-dihydrobenzofuran-5-yl] acrylic acid.

A solution of ethyl 3-[3-methyl-3-(3,5,5,8,8-pentamethyl-5,6,7,8-tetrahydronaphthalen-2-yl)-2,3-dihydrobenzofuran-5-yl]acrylate (320 mg, 0.74 mmol), water (40 µl) and sodium hydroxide (240 mg, 6 mmol) in THF is heated to reflux for 24 h. The reaction mixture is poured onto an AcOEt/water mixture, acidified to pH=1 with a concentrated hydrochloric acid solution, and extracted once with ethyl acetate. After separation the organic phase is washed twice with water, dried over magnesium sulphate and concentrated in vacuo at 40° C. in a rotary evaporator. The solid obtained is crystallized in heptane.

White solid. Mass: 300 mg. Yield: 100%. M.p. 190° C.

$^1$H [lacuna] NMR (CDCl$_3$): 1.24 to 1.27 (12H, m), 1.68 (4H, s), 1.77 (3H, s), 1.95 (3H, s), 4.50 (1H, d, J=9.1 Hz), 4.79 (1H, d, J=9.1 Hz), 6.22 (1H, d, J=—5.9 Hz), 6.85 (1H Ar, d, J=8.3 Hz), 7.03 (1H Ar, s), 7.17 (1H Ar, s), 7.31 (1H Ar, s), 7.37 (1H Ar, d, J=8.3 Hz), 7.70 (1H, d, J=15.9 Hz).

$^{13}$C [lacuna] NMR (CDCL$_3$): 21.1, 29.2, 31.5, 31.7, 31.8, 31.9, 33.6, 33.9, 35.0, 35.1, 49.4, 84.8, 109.8, 115.7, 123.4, 125.0, 127.4, 129.5, 130.6, 133.1, 137.1, 138.7, 141.7, 143.4, 144.5, 161.4, 168.9, 186.4.

Example 10 ethyl 3-[3-methyl-3-(naphthalen-2-yl)-2,3-dihydrobenzofuran-5-yl]acrylate a) Methyl 3-iodo-4-[2-(naphthalen-2-yl)-2-oxoethoxy]benzoate.

The experimenal procedure is analogous to that followed for Example 1c applied to methyl 2-bromo-1-naphthalen-2-yl-ethanone and 4-hydroxy-3-iodobenzoate.

Beige solid. Mass: 14.7 g. Yield: 91%.

$^1$H [lacuna] NMR (CDCl$_3$): 3.88 (3H, s), 5.51 (2H, s) 6.77 (1H, d, J=8.7 Hz), 7.58 to 8.05 (8H Ar, m), 8.48 (1H Ar, d, J=2.05 Hz).

b) Methyl 3-iodo-4-[2-(naphthalen-2-yl)allyl-oxy]benzoate

The experimental procedure is analogous to that followed for Example 1d applied to methyl 3-Iodo-4-[2-(naphthalen-2-yl)-2-oxoethoxy)benzoate.

Yellow solid. Mass: 2.9 g. Yield: 20%.

$^1$H [lacuna] NMR (CDCl$_3$): 3.88 (3H, s), 5.12 (2H, s) 5.71 (1H, s), 5.80 (1H, s), 6.92 (1H, d, J=8.7 Hz), 7.48 to 7.52 (2H Ar, m), 7.63 (1H Ar, dd, J=1.8 Hz, 9.7 Hz), 7.852 to 7.99 (3H Ar, m), 8.01 (!H Ar, dd, J=8.7 Hz), 8.48 (1H Ar, d, J=2.2 Hz).

c) methyl 3-methyl-3-naphthalen-2-yl-2,3-dihydrobenzofuran-5-carboxylate.

The experimental procedure is analogous to that followed for Example 1e applied to methyl 3-Iodo- 4-[2-(naphthalen-2-yl)allyloxy]benzoate.

Colourless oil. Mass: 1 g. Yield: 48%.

$^1$H [lacuna] NMR (CDCl$_3$): 1.89 (3H, s), 3.88 (3H, s) 4.62 (1H, d, J=8.9 Hz), 4.80 (1H, d, J=8.9 Hz), 6.93 (1H, d, J=8.5 Hz), 7.34 (1H, dd, J=2 Hz, J=8.7 Hz), 7.45 to 7.49 (2H, m), 7.71 to 7.73 (2H, m), 7.78 to 7.82 (3H, m), 7.97 (1H, dd, J=1.8 Hz, J=8.5 Hz).

d) 3-methyl-3-naphthalen-2-yl-2,3-dihydrobenzofuran-5-carbaldehyde

The experimental procedure is analogous to that followed for Example 8d applied to methyl 3-Iodo-4-[2-(naphthalen-2-yl)allyloxy]benzoate.

Colourless oil. Mass: 770 mg. Yield: 85%.

$^1$H [lacuna] NMR (CDCl$_3$): 1.91 (3H, s), 4.67 (1H, d, J=9 Hz), 4.85 (1H, d, J=9 Hz), 7.02 (1H, d, J=8.3 Hz), 7.36 (1H, dd, J=2 Hz, J=8.7 Hz), 7.46 to 7.50 (3H, m), 7.60 (1H, d, J=1.7 Hz), 7.74 to 7.82 (4h, m), 8.82 (1H, s).

d) ethyl 3-[3-methyl-3-(naphthalen-2-yl)-2,3-dihydrobenzofuran-5-yl]acrylate

The experimental procedure is analogous to that followed for Example 1i applied to 3-methyl-3-(naphthalen-2-yl)-2,3-dihydrobenzofuran-5-carbaldehyde.

Colourless oil. Mass: 320 mg. Yield: 79%.

$^1$H [lacuna] NMR (CDCl$_3$): 1.28 (3H, t, J=7 Hz), 1.88 (3H, s), 4.20 (2H, q, J=7 Hz), 4.59 (1H, d, J=8.9 Hz), 4.76 (1H, d, J=8.9 Hz), 6.23 (1H, d, J=16 Hz), 6.92 (1H, d, J=8.3 Hz), 7.21 (1H, d, J=1.7 Hz), 7.35 to 7.49 (4H, m), 7.61 (1H, d, J=15.9 Hz), 7.74 to 7.82 (4H, m).

Example 11

3-[3-Methyl-3-(naphthalen-2-yl)-2,3-dihydrobenzofuran-5-yl]acrylic acid.

The experimental procedure is analogous to that followed for Example 9 applied to ethyl 3-[3-methyl-3-(naphthalen-2-yl)-2,3-dihydrobenzofuran-5-yl]acrylate.

Colourless oil. Mass: 650 mg. Yield: 97%. M.p.=160° C.

$^1$H [lacuna] NMR (CDCl$_3$): 1.88 (3H, s), 4.59 (1H, d, J=8.9 Hz), 4.76 (1H, d, J=8.9 Hz), 6.21 (1H, d, J=15.9 Hz), 6.92 (1H, d, J=8.3 Hz), 7.22 (1H, s), 7.33 to 7.93 (9H, m).

Example 12 ethyl 3-[3-(8,8-dimethyl-5,6,7,8-tetrahydronaphthalen-2-yl)-3-methyl-2,3-dihydrobenzofuran-5-yl]acrylate a) methyl 4-[2-(8,8-dimethyl-5,6,7,8-tetrahydronaphthalen-2-yl)-2-oxoethoxy]-3-iodobenzoate.

The experimental procedure is analogous to that followed for Example 1c applied to 5,6,7,8-tetrahydro-8,8-dimethyl-2-bromoacetonaphthone and to methyl 4-hydroxy-3-iodobenzoate.

Beige solid. Mass: 18.7 g. Yield: 64%. M.p.=120° C.

$^1$H [lacuna] NMR (CDCl$_3$): 1.31 (5H, s), 1.66 to 1.71 (2H, m), 1.79 to 1.89 (2H, m), 2.82 (2H, t, J=6.1 Hz), 3.88 (3H, s), 5.39 (2H, s), 6.71 (1H Ar, d, J=8.8 Hz), 7.16 (1H Ar, d, J=8.0 Hz), 7.69 (1H Ar, dd, J=1.7 Hz, J=8.0 Hz), 7.93 (1H Ar, dd, J=8.8 Hz, J=2.0 Hz), 7.99 (1H Ar, d, J=1.7 Hz), 8.47 (1H Ar, d, J=2.0 Hz).

b) methyl 4-[2-(8,8-dimethyl-5,6,7,8-tetrahydronaphthalen-2-yl)allyloxy]-3-iodobenzoate.

The experimental procedure is analogous to that followed for Example 1d applied to methyl 4-[2-(8,8-dimethyl-5,6,7,8-tetrahydronaphthalen-2-yl)-2-oxoethoxy]-3-iodobenzoate.

Colourless oil. Mass: 11 g. Yield: 59%.

$^1$H [lacuna] NMR (CDCl$_3$): 1.30 (6H, s), 1.65 to 1.69 (2H, m), 1.77 to 1.86 (2H, m), 2.77 (2H, t, J=6.1 Hz), 3.89 (3H, s), 4.99 (2H, s), 5.55 (1H, s), 5.57 (1H, s), 6.87 (1H Ar, d, J=8.6 Hz), 7.05 (1H Ar, d, J=7.9 Hz), 7.17 (1H Ar, dd, J=7.9 Hz, J=1.8 Hz), 7.40 (1H Ar, d, J=1.8 Hz), 7.99 (1H Ar, dd, J=8.6 Hz, J=2.1 Hz), 8.47 (1H Ar, d, J=2.1 Hz).

c) methyl 3-(8,8-dimethyl-5,6,7,8-tetrahydronaphthalen-2-yl)-3-methyl-2,3-dihydrobenzofuran-5-carboxylate.

The experimental procedure is analogous to that followed for Example 1e applied to methyl 4-[2-(8,8-dimethyl-5,6,7,8-tetrahydronaphthalen-2-yl)allyloxy]-3-iodobenzoate.

Yellow oil. Mass: 4.2 g. Yield: 52%.

$^1$H [lacuna] NMR (CDCl$_3$): 1.22 (3H, s), 1.25 (3H, s) 1.62 to 1.66 (2H, m), 1.75 (3H, s), 1.77 to 1.83 (2H, m), 2.73 (2H, t, J=6.3 Hz), 3.84 (3H, 5), 4.54 (1H, d, J=8.8 Hz), 4.66 (1H, d, J=8.8 Hz), 6.89 (1H Ar, d, J=8.5 Hz), 6.9 to 7.00 (2H Ar, m), 7.25 (1H Ar, d, J=1.8 Hz), 7.72 (1H Ar, d, J=1.8 Hz), 7.93 (1H Ar, dd, J=8.4,J=1.9 Hz).

$^{13}$C [lacuna] NMR (CDCl$_3$) d: 19.61 (CH$_2$), 26.41 (CH$_3$), 30.26 (CH$_2$TTNN), 31.84 and 31.87 (CH$_3$ TTNN), 34.00 (C TTNN), 39.25 (CH$_2$ TTNN), 49.33 (C), 57.76 (OCH$_3$), 87.19 (CH$_2$O), 109.62 (CH Ar), 123.20 (C Ar), 123.51 (CH Ar), 124.32 (CH Ar), 126.13 (CH Ar), 129.20 (CH Ar), 131.23 (CH Ar), 134.70 (C Ar), 136.44 (C Ar), 142.92 (C Ar), 145.88 (C Ar), 163.68 (C—O Ar), 166.89 (COO).

d) 3-(8,8-dimethyl-5,6,7,8-tetrahydronaphthalen-2-yl)-3-methyl-2,3-dihydrobenzofuran-5-carbaldehyde.

The experimental procedure is analogous to that followed for Example 8d applied to methyl 3-(8,8-dimethyl-5,6,7,8-tetrahydronaphthalen-2-yl)-3-methyl-2,3-dihydrobenzofuran-5-carboxylate.

Colourless oil. Mass: 1.7 g. Yield: 93%.

$^1$H [lacuna] NMR (CDCl$_3$): 1.21 (3H, s), 1.26 (3H, s), 1.62 to 1.67 (2H, m), 1.76 (3H, s), 1.76 to 1.83 (2H, m), 2.73

(2H, t, J=6.2 Hz), 4.58 (1H, d, J=8.9 Hz), 4.72 (1H, d, J=8.9 Hz), 6.91 to 7.01 (3H Ar, m), 7.24 (1H Ar, d, J=1.8 Hz), 7.57 (1H Ar, d, J=1.7 Hz), 7.74 (1H Ar, dd, J=1.8 Hz, J=8.3 Hz), 9.82 (1H, s).

e) ethyl 3-[3-(8,8-dimethyl-5,6,7,8-tetrahydronaphthalen-2-yl)-3-methyl-2,3-dihydrobenzofuran-5-yl]acrylate.

The experimental procedure is analogous to that followed for Example 1i applied to 3-(8,8-dimethyl-5,6,7,8-tetrahydronaphthalen-2-yl)-3-methyl-2,3-dihydrobenzofuran-5-carbaldehyde.

Colourless oil. Mass: 1.97 g. Yield: 95%.

$^1$H [lacuna] NMR (CDCl$_3$): 1.22 to 1.33 (9H, m), 1.62 to 1.67 (2H, m), 1.74 (3H, s), 1.74 to 1.81 (2H, m), 2.73 (2H, t, J=6.4 Hz), 4.21 (2H, q, J=7.1 Hz), 4.50 (1H, d, J=8.7 Hz), 4.62 (1H, d, J=8.7 Hz), 6.23 (1H, d, J=15.9 Hz), 6.88 (1H Ar, d, J=8.3 Hz), 6.96 to 7.01 (2H, Ar, m), 7.20 (1H Ar, d, J=1.8 Hz), 7.26 (1H, s), 7.36 (1H Ar, dd, J=1.8 Hz, J=8.3 Hz), 7.61 (1H Ar, d, J=15.9 Hz).

$^{13}$C [lacuna] NMR (CDCl$_3$): 14.3, 19.6, 26.3, 30.3, 31.9, 34.0, 39.2, 49.5, 60.3, 87.0, 110.2, 115.2, 123.6, 124.4, 127.9, 129.2, 129.7, 134.8, 137.1, 142.9, 144.7, 145.9, 161.7, 167.4.

Example 13

3-[3-(8,8-Dimethyl-5,6,7,8-tetrahydronaphthalen-2-yl)-3-methyl-2,3-dihydrobenzofuran-5-yl]acrylic acid The experimental procedure is analogous to that followed for Example 9 applied [lacuna] ethyl 3-[3-(8,8,-dimethyl-5,6,7,8-tetrahydronaphthalen-2-yl)-3-methyl-2,3-dihydrobenzofuran-5-yl]acrylate.

White solid. Mass: 650 mg. Yield: 97%. M.p.=160° C.

$^1$H [lacuna] NMR (CDCl$_3$): 0.98 (3H, s), 1.01 (3H, s) 1.38 to 1.43 (2H, m), 1.51 (3H, s), 1.51 to 1.57 (2H, m), 2.49 (2H, t, J=6.1 Hz), 4.27 (1H, d, J=8.7 Hz), 4.38 (1H, d, J=8.7 Hz), 5.97 (1H, d, J=15.9 Hz), 6.63 (1H Ar, d, J=8.3 Hz), 6.68 to 6.77 (2H Ar, m), 6.97 (1H Ar, d, J=1.6 Hz), 7.00 (1H, s), 7.12 (1H, d, J=1.7 Hz, J=8.3 Hz), 7.33 (1H Ar, d, J=15.9 Hz).

$^{13}$C [lacuna] NMR (CDCl$_3$): 20.1, 26.8, 30.1, 32.3, 34.4, 39.7, 49.9, 87.0, 110.8, 114.7, 124.0, 124.5, 124.8, 127.9, 129.7, 130.6, 135.2, 137.7, 143.2, 146.3, 147.5, 162.6, 173.5.

Example 14 ethyl 3-[3-(5,5-dimethyl-5,6,7,8-tetrahydronaphthalen-2-yl)-3-methyl-2,3-dihydrobenzofuran-5-yl]acrylate.

a) 5,6,7,8-tetrahydro-3-bromo-5,5-dimethyl-2-bromoacetonaphthone

A solution of bromoacetyl bromide (24.7 g, 0.28 mol) in 200 ml of CH$_2$Cl$_2$ is added dropwise to a solution of aluminium chloride (51.5 g, 0.39 mol) in 100 ml of CH$_2$Cl$_2$ at 0° C. The mixture is stirred for 1 h at 0° C., then a solution of 5,6,7,8-tetrahydro-3-bromo-5,5-dimethyl-2-acetonaphthone (60 g, 0.25 mol) in CH$_2$Cl$_2$ (100 ml) is added dropwise. The stirring is continued for 2 h and then the mixture is poured onto water and ice and extracted with CH$_2$Cl$_2$. The organic phase is washed twice with water, dried over magnesium sulphate and concentrated in vacuo in a rotary evaporator.

Pale oil. Mass: 90 g. Yield: quantitative.

$^1$H [lacuna] NMR (CDCl$_1$): 1.28 (6H, s), 1.63 to 1.68 (2H, m), 1.76 to 1.84 (2H, m), 2.73 (2H, t, J=6 Hz), 3.88 (3H, s), 5.26 (2H, s), 6.72 (1H Ar, d, J=8.6 Hz), 7.24 (1H Ar, s), 7.53 (1H Ar, s), 7.97 (1H Ar, dd, J=2.0 Hz, J=8.6 Hz), 8.44 (1H Ar, d, J=2.0 Hz).

b) methyl 4-[2-(3-bromo-5,5-dimethyl-5,6,7,8-tetrahydronaphthalen-2-yl)-2-oxoethoxy]-3-iodobenzoate The experimental procedure is analogous to that followed for Example 1c applied to 5,6,7,8-tetrahydro-3-bromo-5,5-dimethyl-2-bromoacetonaphthone and to methyl 4-hydroxy-3-iodobenzoate.

Yellow solid. Mass: 20 g. Yield: 26%. M.p.=142° C.

$^1$H [lacuna] NMR (CDCl$_3$): 1.28 (6H, s), 1.63 to 1.68 (2H, m), 1.76 to 1.84 (2H, m), 2.73 (2H, t, J=6 Hz), 3.88 (3H, s), 5.26 (2H, s), 6.72 (1H Ar, d, J=8.6 Hz), 7.24 (1H Ar, s), 7.53 (1H Ar, s), 7.97 (1H Ar, dd, J=2.0 Hz, J=8.6 Hz), 8.44 (1H Ar, d, J=2.0 Hz).

c) methyl 4-[2-(3-bromo-5,5-di-methyl-5,6,7,8-tetrahydronaphthalen-2-yl)allyloxy]-3-iodobenzoate.

The experimental procedure is analogous to that followed for Example 1d applied to methyl 4-[2-(3-bromo-5,5-dimethyl-5,6,7,8-tetrahydronaphthalen-2-yl)-2-oxoethoxy]-3-iodobenzoate.

Yellow solid. Mass: 5.6 g. Yield: 32%. M.p.=108° C.

$^1$H [lacuna] NMR (CDCl$_3$): 1.28 (6H, s), 1.62 to 1.66 (2H, m), 1.77 to 1.81 (2H, m), 2.69 (2H, t, J=6 Hz), 3.89 (3H, s), 4.86 (2H, s), 5.28 (1H, s), 5.70 (1H, s), 6.87 (1H Ar, d, J=8.7 Hz), 6.98 (1H Ar, s), 7.49 (1H Ar, s), 7.98 (1H Ar, dd, J=2.0 Hz, J=8.7 Hz), 8.45 (1H Ar, d, J=2.0 Hz).

d) methyl 3-(5,5-dimethyl-5,6,7,8-tetrahydronaphthalen-2-yl)-3-methyl-2,3-dihydrobenzofuran-5-carboxylate.

The experimental procedure is analogous to that followed for Example 1e applied to methyl 4-[2-(3-bromo-5,5-dimethyl-5,6,7,8-tetrahydronaphthalen-2-yl)-allyloxy]-3-iodobenzoate doubling the molar equivalents of tributylamine and formic acid.

Yellow oil. Mass: 4.2 g. Yield: 52%.

$^1$H [lacuna] NMR (CDCl$_3$): 1.18 (6H, s), 1.55 to 1.59 (2H, m), 1.66 (3H, s), 1.69 to 1.74 (2H, m), 2.61 (2H, t, J=6 Hz), 3.78 (3H, s), 4.44 (1H, d, J=8.8 Hz), 4.61 (1H, d, J=8.8 Hz), 6.88 (1H Ar, d, J=8.4 Hz), 6.91 (1H Ar, s), 7.01 (1H Ar, dd, J=2.2 Hz, J=8.3 Hz), 7.23 to 7.27 (2H Ar, m), 7.74 (1H Ar, d, J=2.2 Hz), 7.93 (1H Ar, dd, J=8.4, J=2.2 Hz).

e) 3-(5,5-dimethyl-5,6,7,8-tetrahydronaphthalen-2-yl)-3-methyl-2,3-dihydrobenzofuran-5-carbaldehyde.

The experimental procedure is analogous to that followed for Example 8d applied to methyl 3-(5,5-dimethyl-5,6,7,8-tetrahydronapthalen-2-yl)-3-methyl-2,3-dihydrobenzofuran-5-carboxylate.

Colourless oil. Mass: 400 mg. Yield: 62%.

$^1$H [lacuna] NMR (CDCl$_3$): $^1$H [lacuna] NMR (CDCl$_3$): 1.18 (3H, s), 1.19 (3H, s), 1.53 to 1.58 (2H, m), 1.67 (3H, s), 1.67 to 1.74 (2H, m), 2.65 (2H, t, J=6.3 Hz), 4.48 (1H, d, J=9 Hz), 4.66 (1H, d, J=9 Hz), 6.76 to 6.96 (3H, m), 6.18 (1H Ar, d, J=8.3 Hz), 7.51 (1H Ar, d. J=1.8 Hz), 7.65 (1H Ar, dd, J=1.S Hz, J=8.3 Hz), 9.75 (1H, s).

f) ethyl 3-[3-(5,5-dimethyl-5,6,7,8-tetrahydronaphthalen-2-yl)-3-methyl-2,3-dihydrobenzofuran-5-yl]acrylate The experimental procedure is analogous to that followed for Example 1i applied to 3-(5,5-dimethyl-5,6,7,8-tetrahydronaphthalen-2-yl)-3-methyl-2,3-dihydrobenzofuran-5-carbaldehyde.

Colourless oil. Mass: 400 mg. Yield: 78%.

$^1$H [lacuna] NMR (CDCl$_3$): 1.26 to 1.33 (9H, s), 1.62 to 1.66 (2H, m), 1.72 (3H, s), 1.76 to 1.79 (2H, m), 2.72 (2H, t, J=6.2 Hz), 4.22 (2H, q, J=7 Hz), 4.48 (1H, d, J=8.8 Hz), 4.65 (1H, d, J=8.8 Hz), 6.24 (1H, d, J=15.9 Hz), 6.72 (1H Ar, d, J=8.3 Hz), 6.85 (1H Ar, s), 7.01 (1H Ar, d), 7.20 to 7.27 (2H Ar, m), 7.35 (1H, d, J=8.3 Hz), 7.61 (1H Ar, d, J=15.9 Hz).

Example 15

3-[3-(5,5-Dimethyl 5,6,7,8-tetrahydronaphthalen-2-yl)-3-methyl-2,3-dihydrobenzofuran-5-yl]acrylic acid.

The experimental procedure is analogous to that followed for Example 9 applied to ethyl 3-[3-(5,5-dimethyl-5,6,7,8-tetrahydronaphthalen-2-yl)-3-methyl-2,3-dihydrobenzofuran-5-yl]acrylate.

White solid. Mass: 160 mg. Yield: 43%. M.p.=142° C.

¹H [lacuna] NMR (CDCl₃): 1.26 (6H, s), 1.62 to 1.66 (2H, m), 1.73 (3H, s), 1.72 to 1.79 (2H, m), 2.72 (2H, t, J=6.2 Hz), 4.49 (1H, d, J=8.8 Hz), 4.66 (1H, d, J=8.8 Hz), 6.25 (1H, d, J=15.9 Hz), 6.88 (1H Ar, d, J=8.3 Hz), 6.94 (1H Ar, s), 7.02 (1H Ar, d), 7.25 to 7.28 (2H Ar, m), 7.38 (1H, d, J=8.3 Hz), 7.71 (1H, d, J=15.9 Hz).

Example 16 ethyl 3-[3-methyl-3-(5,5,8,8-tetramethyl-5,6,7,8-tetrahydronaphthalen-2-yl)-2,3-dihydrobenzofuran-6-yl]-acrylate.

a) 4-Iodo-3-hydroybenzoic acid.

A 3.6% sodium perchlorate solution is added dropwise to a mixture of 4-hydroxybenzoic acid (2.55 g, 18.5 mmol), sodium hydroxide (0.74 g, 18.5 mmol), sodium iodide (2.77 g, 18.5 mmol) in methanol (50 ml) at 0° C. The mixture is stirred for two hours at 0° C. 20 ml of a 10% sodium thiosulphate solution are added. After stirring, the mixture is acidified to pH 1 with hydrochloric acid. It is extracted with 100 ml of ethyl ether. The organic phase is washed twice with 80 ml of water, dried over magnesium sulphate and concentrated in vacuo at 40° C. in a rotary evaporator.

White solid. Mass: 2.71 g, Yield: quantitative.

M.p.: 178–185° C.

¹H [lacuna] NMR (DMSO, 250 MHz): 7.13 (1H Ar, dd, J=1.08 Hz, J=7.55 Hz), 7.41 (1H Ar, d, J=1.08 Hz), 7.76 (1H Ar, d, J=7.55 Hz), 10.71 (1H, s), 12.96 (1H, s).

b) Methyl 4-iodo-3-hydroybenzoate.

A solution of 4-iodo 3-hydroxybenzoic acid (2.71 g, 10 mmol) and sulphuric acid (0.7 ml) in methanol (17 ml) is heated to reflux for 6 h. 20 ml of water are added and the mixture is alkalinized to neutrality with sodium bicarbonate. It is extracted with ethyl ether (60 ml). The organic phase is washed with twice 30 ml of water, dried over magnesium sulphate, and concentrated in vacuo at 40° C. in a rotary evaporator. The product is purified by flash chromatography on a silica column (ethyl acetate 50%, heptane 50%).

White solid. Mass: 2 g. Yield: 72%. M.p.: 164° C.

¹H [lacuna] NMR (CDCl₃, 250 MHz): 3.91 (3H, s), 5.70 (1H, s), 7.33 (1H Ar, d, J=8.16 Hz), 7.64 (1H Ar, s), 7.75 (1H Ar, d, J=8.16 Hz).

c) Methyl 4-iodo-3-[2-oxo-2-(5,5,8,8-tetramethyl-5,6,7,8-tetrahydronaphthalen-2-yl)ethoxy]-benzoate.

The experimental procedure is analogous to that Followed for Example 1c applied to 5,6,7,8-tetrahydro-5,5,8,8-tetramethyl-2-bromoacetonaphthone and to methyl 3-hydroxy-4-iodobenzoate.

White solid. Mass: 1.69 g, Yield: 81%. M.p.: 124° C.

¹H [lacuna] NMR (CDCL₃, 250 MHz): 1.31 (6H, s), 1.32 (6H, s), 1.71 (4H, s), 3.88 (3H, s), 5.42 (2H, s), 7.35 to 7.41 (2H Ar, m), 7.43 (1H Ar, d, J=8.25 Hz), 7.74 (1H Ar, dd, J=8.25,J=2.5 Hz), 7.90 (1H Ar, d, J=7.5 Hz)7.98(1H Ar, d, J=2.5 Hz).

d) Methyl 4-iodo-3-[2-(5,5,8,8-tetramethyl-5,6,7,8-tetrahydronaphthalen-2-yl)allyloxy]benzoate.

The experimental procedure is analogous to that followed for Example 1d applied to methyl 4-Iodo- 3-[2-oxo-2-(5,5,8,8-tetramethyl-5,6,7,8-tetrahydronaphthalen-2-yl)ethoxy] benzoate. The product is purified by flash chromatography on a silica column (CH₂Cl₂ 60%, heptane 40%).

White solid. Mass: 0.69 g, Yield: 42%. M.p.: 53° C.

¹H [lacuna] NMR (CDCL₃, 250 MHz): 1.29 (6H, s),1.30 (6H, s), 1.69 (4H, s), 3.91 (3H, s), 4.98 (2H, s), 5.58 (2H, s), 7.20 to 7.41 (4H Ar, m), 7.50 (1H Ar, d, J=1.15 Hz), 7.87 (1H Ar, d, J=8.00).

¹³C [lacuna] NMR (CDCL₃, 250 MHz): 31.34, 31.44, 33.71, 33.88, 34.55, 34.69, 51.86, 70.47, 92.84, 112.25, 113.66, 123.01, 123.06, 123.89, 131.08, 135.05, 139.12, 142.01, 144.53, 156.85, 166.05.

e) methyl 3-methyl-3-(5,5,8,8-tetramethyl-5,6,7,8-tetrahydronaphthalen-2-yl)-2,3-dihydrobenzofuran-6-carboxylate.

The experimental procedure is analogous to that followed for Example 1e applied to methyl 4-Iodo-3-(2-(5,5,8,8-tetramethyl-5,6,7,8-tetrahydronaphthalen-2-yl)allyloxy] benzoate.

The product is purified by flash chromatography on a silica column (CH₂Cl₂ 60% heptane 40%)

White solid. Mass: 330 mg, Yield: 68%. M.p.: 121° C.

¹H [lacuna] NMR (CDCL₃, 250 MHz) 1.20 (3H, s), 1.22 (3H, s), 1.25 (6H, s), 1.66 (4H, s), 1.73 (3H, s), 3.91 (3H, s), 4.48 (1H, d, J=8.75 Hz), 4.62 (1H, d, J=8.75 Hz), 7.00 (1H, dd, J=2 Hz, J=8.25 Hz), 7.09 (1H Ar, d, J=8 Hz), 7.18 to 7.24 (2 H Ar, m), 7.52 (1H Ar, s), 7.63 (1H Ar, d, J=8.00 Hz).

¹³C [lacuna] NMR (CDCL₃, 250 MHz): 26.16, 31.77, 31.87, 33.96, 34.37, 35.01, 35.10, 49.79, 52.09, 86.48, 110.82, 122.84, 123.67, 123.93, 124.30, 126.60, 130.56, 141.35, 142.15, 143.32, 144.88, 159.80, 166.97.

f) 3-methyl-3-(5,5,8,8-tetramethyl-5,6,7,8-tetrahydronaphthalen-2-yl)-2,3-dihydrobenzofuran-6-carbaldehyde.

The experimental procedure is analogous to that followed for Example 8d applied to methyl 3-methyl-3-(5,5,8,8-tetramethyl-5,6,7,8-tetrahydronaphthalen-2-yl)-2,3-dihydrobenzofuran-6-carboxylate.

Colourless oil. Mass: 1.25 9, Yield: 90%.

¹H [lacuna] NMR (CDCL₃, 250 MHz): 1.20 (3H, s), 1.23 (3H, s), 1.26 (5H, s), 1.66 (4H, s), 1.75 (37, s), 4.51 (1H, d, J=8.7 Hz), 4.66 (1H, d, J=8.7 Hz), 7.00 (1H, dd, J=2.1 Hz), J=8.3 Hz), 7.16 to 7.25 (3H Ar, m), 7.36 (1H Ar, d, J=1.3 Hz), 7.44 (1H Ar, dd, J=1.3 Hz, J=7.6 Hz).

g) ethyl 3-[3-methyl-3-(5,5,8,8-tetramethyl-5,6,7,8-tetrahydronaphthalen-2-yl)-2,3-dihydrobenzofuran-6-yl] acrylate.

The experimental procedure is analogous to that followed for Example 1i applied to 3-methyl-3-(5,5,8,8-tetramethyl-5,6,7,8-tetrahydronaphthalen-2-yl)-2,3-dihydrobenzofuran-6-carbaldehyde.

Colourless oil. Mass: 1.4 9. Yield: 94%.

¹H [lacuna] NMR (CDCL₃, 250 MHz): 1.21 (3H, s), 1.23 (3H, s), 1.26 (6H, s), 1.34 (3H, t, J=7.1 Hz), 1.66 (4H, s), 1.73 (3H, s), 4.26 (2H, t, J=7.1 Hz), 4.47 (1H, d, J=8.7 Hz), 4.61 (1H, d, J=8.7 Hz), 6.39 (1H, d, J=16 Hz), 6.98 to 7.06 (4H Ar, m), 7.19 to 7.25 (2H Ar, m), 7.66 (1H, d, J=16 Hz), 9.95 (1H, s).

Example 17

3-[3-Methyl-3-(5,5,8,8-tetramethyl-5,6,7,8-tetrahydronaphthalen-2-yl)-2,3-dihydrobenzofuran-6-yl] acrylic acid.

The experimental procedure is analogous to that followed for Example 9 applied [lacuna] ethyl 3-[3-methyl-3-(5,5,8,8-tetramethyl-5,6,7,8-tetrahydronaphthalen-2-yl)-2,3-dihydrobenzofuran-6-yl]-acrylate.

White solid. Mass: 1.05 g. Yield: 80%. M.p.=190° C. ¹H [lacuna] NMR (CDCL₃, 250 MHz): 1.22 (3H, s), 1.23 (3H, s), 1.26 (6H, s), 1.66 (4H, s), 1.73 (3H, s), 4.48 (1H, d, J=8.7 Hz), 4.62 (1H, d, J=8.7 Hz), 6.42 (1H, d, J=16 Hz), 6.98 to 7.09 (4H Ar, m), 7.20 to 7.25 (2H Ar, m), 7.78 (1H, d, J=16 Hz).

Example 18 ethyl 3-[3-allyl-3-(5,5,8,8-tetramethyl-5,6,7,8-tetrahydronaphthalen-2-yl)-2,3-dihydrobenzofuran-5-yl]-acrylate a) methyl 3-[3-allyl-3-(5,5,8,8-tetramethyl-5,6,7,8-tetrahydronaphthalen-2-yl)-2,3-dihydrobenzofuran-5-yl]carboxylate A mixture of palladium diacetate (345 mg, 0.46 mmol), tributylvinyltin (1.3 ml, 4.56 mmol), tributylamine (675 µl, 4.56 mmol) and methyl 3-Iodo-4-[2-[5,6,7,8-tetrahydro-5,5,8,8-tetramethyl-2-naphthyl]-1-propenyloxybenzoate (2.3 g, 4.56 mmol) in acetonitrile (50 ml) is heated at 70° C. for 8 d adding tributylvinyltin (0.8 ml) again every 24 h. The reaction mixture is concentrated in vacuo at 40° C. in a rotary evaporator and treated with water and ethyl ether. After separation, the organic phase is washed twice with 40 ml of water, dried over magnesium sulphate, and concentrated in vacuo at 40° C. in a rotary evaporator.
The product is purified by flash chromatography on a silica column (CH$_2$Cl$_2$ 70% heptane 30%)

Colourless oil. Mass: 1.13 g. Yield 61%.

$^1$H [lacuna] NMR (CDCL$_3$, 250 MHz): 1.22 to 1.26 (12H, m) 1.69 (4H, s), 2.88 (2H, d, J=7.3 Hz), 3.86 (3H, s), 4.63 (1H, d, J=9 Hz), 4.69 (1H, d, J=9 Hz), 5.03 (1H, s), 5.08 (1H, d, J=5.4), 5.58 (1H, m), 6.84 to 6.90 (2H Ar, m), 7.20 to 7.24 (2H Ar, m), 7.91 (1H Ar, d, J=1.9 Hz), 7.93 (1H Ar, dd, J=1.8 Hz, J=8.3 Hz).

b) 3-[3-allyl-3-(5,5,8,8-tetramethyl-5,6,7,8-tetrahydronaphthalen-2-yl)-2,3-dihydrobenzofuran-5-yl]-carbaldehyde The experimental protocol is analogous to that followed for Example 8d applied to methyl 3-[3-Allyl-3-(5,5,8,8-tetramethyl-5,6,7,8-tetrahydronaphthalen-2-yl)-2,3-dihydrobenzofuran-5-yl]-carboxylate. The product is purified by flash chromatography on a silica column (AcOEt 10% heptane 90%).

Colourless oil. Mass: 670 mg, Yield: 39%.

$^1$H [lacuna] NMR (CDCL$_3$, 250 MHz): 1.22 to 1.26 (12H, m) 1.67 (4H, s), 2.88 (2H, t, J=7.3 Hz), 4.68 (1H, d, J=9.1 Hz), 4.73 (1H, d, J=9.1 Hz), 5.04 (1H, s), 5.08 (1H, s), 5.57 (1H, m), 6.93 to 7.01 (2H Ar, m), 7.21 to 7.25 (2H Ar, m), 7.64 (1H Ar, d, J=1.7 Hz), 7.25 (1H Ar, dd, J=1.8 Hz, J=8.3 Hz), 9.87 (1H, s).

c) ethyl 3-[3-allyl-3-(5,5,8,8-tetramethyl5,6,7,8-tetrahydronaphthalen-2-yl)-2,3-dihydrobenzofuran-5-yl]acrylate The experimental procedure is analogous to that followed for Example 1i applied to 3-[3-allyl-3-(5,5,8,8-tetramethyl-5,6,7,8-tetrahydronaphthalen-2-yl)-2,3-dihydrobenzofuran-5-yl]carbaldehyde. The product is purified by flash chromatography on a silica column (AcOEt 80% heptane 80%)

Colourless oil. Mass: 790 mg, Yield: 99%.

$^1$H [lacuna] NMR (CDCL$_3$, 250 MHz): 1.18 to 1.34 (15H, m), 1.67 (4H, s), 2.86 (2H, t, J=7.6 Hz), 4.23 (2H, q, J=7 Hz), 4.58 (1H, d, J=9 Hz), 4.64 (1H, d, J=9 Hz), 5.03 (1H, s), 5.08 (1H, d, J=3 Hz), 5.80 (1H, m), 6.25 (1H, d, 15.9 Hz), 6.85 (1H Ar, d, J=8.3 Hz), 7.00 (1H Ar, dd, J=2 Hz, J=8.3 Hz), 7.21 to 7.27 (3H Ar, m), 7.37 (1H Ar, dd, J=1.8 Hz, J=8.3 Hz), 7.67 (1H Ar, d, J=15.8 Hz).

Example 19

3-[3-Allyl-3-(5,5,8,8-tetramethyl-5,6,7,8-tetrahydronaphthalen-2-yl)-2,3-dihydrobenzofuran-5-yl] acrylic acid A solution of ethyl 3-[3-allyl-3-(5,5,8,8-tetramethyl-5,6,7,8-tetrahydronaphthalen-2-yl)-2,3-dihydrobenzofuran-5-yl]acrylate (790 mg, 1.78 mmol) and sodium hydroxide (720 mg, 17.8 mmol) in THF (20 ml) is heated to reflux for 24 h. The mixture is treated with water and ethyl acetate, and acidified to pH 1 with a concentrated hydrochloric acid solution. After separation, the organic phase is washed twice with water, dried over magnesium sulphate, and concentrated in vacuo at 40° C. in a rotary evaporator. The solid obtained is washed with heptane.

White solid. Mass: 596 Beg, Yield: 80%. M.p.=170° C.

$^1$H [lacuna] NMR (CDCL$_3$, 250 MHz): 1.23 to 1.26 (12H, m) 1.67 (4H, s), 2.87 (2H, t, J=7.6 Hz), 4.60 (1H, d, J=9 Hz), 4.66 (1H, d, J=9 Hz), 5.04 (1H, s), 5.08 (1H, d, J=3 Hz), 5.58 (1H, m), 6.25 (1H, d, 15.8 Hz), 6.87 (1H, Ar, d, J=8.3 Hz), 7.00 (1H Ar, d, J=8.3 Hz), 7.22 to 7.29 (3H Ar, m), 7.40 (1H Ar, d, J=8.3 Hz), 7.73 (1H, d, J=15.8 Hz).

Example 20 methyl (E)-3-[3-methyl-3-(5,5,8,8-tetramethyl-5,6,7,8-tetrahydronaphthalen-2-yl)-2,3-dihydrobenzofuran-5-yl]-but-2-enaote a) 1-[3-methyl-3-(5,5,8,8-tetramethyl-5,6,7,8-tetrahydronaphthalen-2-yl)-2,3-dihydrobenzofuran-5-yl]ethanone A 1.6M methyllithium solution in ethyl ether (3.4 ml, 5.4 mmol) is added to a solution of 3-Methyl-3-(5,5,8,8-tetramethyl-5,6,7,8-tetrahydronaphthalen-2-yl)-2,3-dihydrobenzofuran-5-carboxylic acid (Example 2) (900 mg, 4.47 mmol) in THF (50 ml) at −20° C. The mixture is stirred for 4 h at −20° C. and is then poured onto ethyl acetate and a 1N hydrochloric acid solution. The organic phase is washed 2 times with water, dried over anhydrous magnesium sulphate and concentrated in vacuo at 40° C. in a rotary evaporator.

Colourless oil. Mass: 880 mg, Yield: 98%.

$^1$H [lacuna] NMR (CDCL$_3$, 250 MHz): 1.21 (3H, s), 1.24 (3H, s), 1.26 (6H, s), 1.66 (4H, s), 1.75 (3H, s), 2.53 (3H, s), 4.53 (1H, d, J=8.8 Hz), 4.68 (1H, d, J=8.7 Hz), 6.90 (1H Ar, d, J=8.3 Hz), 6.98 (1H Ar, dd, J=8.3 Hz, J=2 Hz), 7.20 to 7.25 (2H Ar, m), 7.69 (1H Ar, d, J=1.8 Hz), 7.86 (1H Ar, dd, J=8.3 Hz, J=2 Hz).

$^{13}$C [lacuna] NMR (CDCL$_3$, 250 MHz): 26.5,, 31.8, 31.9, 34.0, 35.0, 35.1, 49.25, 87.3, 109.6, 123.8, 124.2, 125.0, 126.7, 130.6, 131.2, 136.8, 142.2, 143.4, 144.9, 163.9, 196.7.

b) methyl (E)-3-[3-methyl-3-(5,5,8,8-tetramethyl-5,6,7,8-tetrahydronaphthalen-2-yl)-2,3-dihydrobenzofuran-5-yl] but-2-enaote.

A solution of BuLi in hexane 2.5 M (1.74 [lacuna], 4.3 mmol) is added dropwise to a solution of diisopropylamine (639 µl, 4.6 mmol) in THF (10 ml) at −0° C. The mixture is stirred for 15 min at −0° C., then methyl (trimethylsilyl) acetate (850 µl, 5.2 mmol) is added at −78° C. The mixture is stirred for 15 min at −78° C. and then a solution of 1-[3-Methyl-3-(5,5,8,8-tetramethyl-5,6,7,8-tetrahydronaphthalen-2-yl)-2,3-dihydrobenzofuran-5-yl] ethanone (880 mg, 2.43 mmol) in THF (5 ml) is added at −78° C. The reaction mixture is stirred for 1 h at −78° C. and then treated with ethyl acetate and an aqueous ammonium chloride solution. After separation the organic phase is washed twice with water, dried over anhydrous magnesium sulphate and concentrated in vacuo at 40° C. in a rotary evaporator. The product is purified by flash chromatography on a silica column (AcOEt 3%, heptane 97%).

Colourless oil. Mass: 460 mg, Yield: 44%. $^1$H [lacuna] NMR (DMOS, 250 MHz): 1.17 (6H, s), 1.20 (6H, s), 1.60 (4H, s), 1.71 (3H, s), 2.49 (3H, s), 3.64 (3H, s), 4.47 (1H, d, J=8.9 Hz), 4.63 (1H, d, J=8.9 Hz), 6.12 (1H, s), 6.89 (1H Ar, d, J=9.2 Hz), 7.01 (1H Ar, dd), 7.20 to 7.26 (2H Ar, m), 7.43 to 7.46 (2H Ar, m).

Example 21 methyl (Z)-3-[3-methyl-3-(5,5,8,8-tetramethyl-5,6,7,8-tetrahydronaphthalen-2-yl)-2,3-dihydrobenzofuran-5-yl]-but-2-enoate.

The (Z) isomer is separated from the (E) isomer during flash chromatography on a silica column (AcOEt 3%, heptane 97%).

Colourless oil. Mass: 130 mg, Yield: 12%.

$^1$H [lacuna] NMR (DMSO, 250 MHz): 1.16 (3H, s), 1.17 (3H, s), 1.20 (6H, s), 1.60 (4H, s), 1.67 (3H, s), 2.14 (3H, d, J=1.2 Hz), 3.41 (3H, s), 4.46 (1H, d, J=8.8 Hz), 4.59 (1H, d, J=8.8 Hz), 5.88 (1H, d, J=1.2 Hz), 6.82 (1H Ar, d, J=8.1 Hz), 7.00 to 7.10 (3H Ar, m), 7.18 (1H Ar, d, J=2.1 Hz), 7.24 (1H Ar, d, J=8.3 Hz).

Example 22

(E)-3-[3-Methyl-3-(5,5,8,8-tetramethyl-5,6,7,8-tetrahydronaphthalen-2-yl)-2,3-dihydrobenzofuran-5-yl] but-2-enoic acid The experimental procedure is analogous to that followed for Example 9 applied to methyl (E)-3-[3-methyl-3-(5,5,8, 8-tetramethyl-5,6,7,8-tetrahydronaphthalen-2-yl)-2,3-dihydrobenzofuran-5-yl]but-2-enoate.

White solid. Mass: 370 g. Yield: 88%. M.p.=110° C.

$^1$H [lacuna] NMR (CDCL$_3$, 250 MHz): 1.21 (3H, s), 1.24 (3H, s), 1.26 (6H, s), 1.67 (4H, s), 1.74 (3H, s), 2.56 (3H, d, J=1 Hz), 4.48 (1H, d, J=8.7 Hz), 4.60 (1H, d, J=8.7 Hz), 6.10 (1H, d, J=1 Hz), 6.87 (1H Ar, d, J=8.4 Hz), 7.00 (1H Ar, dd, J=2.1 Hz, J=8.3 Hz), 7.20 to 7.22 (2H Ar, m), 7.39 (1H Ar, dd, J=2 Hz, J=7.5 Hz).

$^{13}$C [lacuna] NMR (CDCL$_3$, 250 Mhz): 18.0, 26.1, 31.5, 31.5, 33.7, 34.1, 34.7, 34.8, 49.4, 86.6, 109.5, 113.8, 122.3, 123.5, 124.0, 126.4, 127.0, 134.5, 136.2, 142.1, 143.0, 144.6, 158.2, 160.9, 171.7.

Example 23 ethyl 3-[3-methyl-3-(5,5,8,8-tetramethyl-5,6,7,8-tetrahydronaphthalen-2-yl)-2,3-dihydrobenzo[b]thiophen-5-yl]acrylate.

a) methyl 4-hydroxy-3-nitrobenzoate.

A solution of 4-hydroxy-3-nitrobenzoic acid (10 g, 54.6 mmol) and concentrated sulphuric acid (1.8 ml) in methanol (90 ml) is heated to reflux for 8 h. The reaction mixture is treated with a sodium bicarbonate solution. After extraction with ethyl ether. The organic phase is washed twice with water, dried over magnesium sulphate, and concentrated in vacuo at 40° C. in a rotary evaporator.

Yellow solid. Mass: 10.8 g, Yield: 100%. M.p.=74° C.

b) Methyl 4-dimethylthiocarbamoyloxy-3-nitrobenzoate.

80% NaH (1.93 g, 65.52 mmol) is added to a methyl 4-hydroxy-3-nitrobenzoate solution (10.5 g, 53.25 mmol) in DM-7 (50 ml) at 0° C. Stirring is continued for 30 min and then a dimethylthiocarbamoyl chloride solution (8.56 g, 69.2 mmol) in DMF (50 ml) is added dropwise at 0° C. The mixture is stirred for 24 h at ambient temperature and treated with an aqueous NH4Cl solution and ethyl ether. The organic phase is washed twice with water, dried over magnesium sulphate, and concentrated in vacuo at 40° C. in a rotary evaporator. The product is purified by flash chromatography on a silica column (ethyl acetate 30%, heptane 70%).

White solid. Mass: 10.6 9, Yield: 70%. M.p.=99° C.

c) Methyl 4-dimethylcarbamoylsulphanyl-3-nitrobenzoate.

Methyl 4-dimethylthiocarbamoyloxy-3-nitrobenzoate (10.6 g, 37.3 mmol) is heated at 180° C. for 15 min.

Yellow solid. Mass: 10.6 g, Yield: 100i. M.p.=79° C.

d) methyl 3-amino-4-dimethylcarbamoylsulphanylbenzoate.

A concentrated hydrochloric acid solution is added dropwise at 0° C. to a mixture of iron (12.7 9) and methyl 4-Dimethylthiocarbamoyloxy-3-nitrobenzoate (10.6 g, 37.3 mmol) in ethanol at 0° C. The reaction mixture is stirred at ambient temperature for 5 h and then treated with a sodium bicarbonate solution. After extraction with dichloromethane, the organic phase is washed twice with water, dried over magnesium sulphate, and concentrated in vacuo at 40° C. in a rotary evaporator. The product is purified by flash chromatography on a silica column (ethyl acetate 50%, heptane 50%).

Yellow solid. Mass: 7.1 9, Yield: 75%. M.p.=135° C.

e) methyl 4-dimethylcarbamoylsulphanyl-3-iodobenzoate.

A solution of methyl 3-Amino-4-dimethylcarbamoylsulphanylbenzoate (5.98 g, 23.5 mmol) isopentyl nitrite (16.2 ml) in dilodomethane (138 ml) is heated at 70° C. for 2 h. The diiodomethane is distilled at 10-1 atm.; then the product is purified by flash chromatography on a silica column (CH$_2$Cl$_2$ 90%, heptane 10%).

Yellow solid. Mass: 3.45 g, Yield: 43a;. M.p.=72° C.

f) Methyl 3-iodo-4-mercaptobenzoate.

A mixture of methyl 4-dimethylcarbamoylsulphanyl-3-iodobenzoate (3.9 g, 16.6 mmol), potassium carbonate (2 g,) in methanol is stirred for 12 h at ambient temperature. The mixture is treated with a concentrated hydrochloric acid solution qs pH=1. After extraction with dichloromethane, the organic phase is washed twice with water, dried over magnesium sulphate, and concentrated in vacuo at 40° C. in a rotary evaporator.

Yellow solid. Mass: 2.7 g, Yield: 100%. M.p.=52° C.

g) methyl 2-(5,5,8,8-tetramethyl-5,6,7,8-tetrahydronaphthalen-2-yl) acrylate.

75% NaH (45 mg, 1.4 mmol) is added to a solution of 2-(5,5,8,8-Tetramethyl-5,6,7,8-tetrahydronaphthalen-2-yl) acrylic acid (300 mg, 1.16 mmol) {synthesis described in WO Patent 9206948} in DMF (10 ml). Stirring is continued for 1 h. at ambient temperature, then iodomethane (87 ul, 1.4 mmol) is added dropwise. The mixture is stirred for 1 h. at ambient temperature, and treated with water and ethyl ether. The organic phase is washed twice with water, dried over magnesium sulphate, and concentrated in vacuo at 40° C. in a rotary evaporator. The product is purified by flash chromatography on a silica column (ethyl acetate 20%,heptane 80%).

Yellow solid. Mass: 45 mg, Yield: 95%.

$^1$H [lacuna] NMR (CDCL$_3$, 250 MHz): 1.28 (6H, s), 1.29 (6H, s), 1.69 (4H, s), 3.82 (3H, s), 5.87 (1H, d, J=1.3 Hz), 6.30 (1H, d, J=1.3 Hz), 7.21 (1H Ar, dd, J=2 Hz, J=8 Hz), 7.29 (1H Ar, d, J=8 Hz), 7.35 (1H Ar, d, J=2 Hz).

h) 2-(5,5,8,8-tetramethyl-5,6,7,8-tetrahydronaphthalen-2-yl)prop-2-en-1-ol

A 1M diisobutylaluminium hydride solution in toluene (2.78 ml, 2.78 mmol) is added at 78° C., dropwise, to a solution of methyl 2-(5,5,8,8-Tetramethyl-5,6,7,8-tetrahydronaphthalen-2-yl)acrylate (310 mg, 1.14 mmol) in dichloromethane (3 ml). The solution is stirred for 1 h at 0° C., then treated with a solution of double tartrate of sodium [lacuna] and filtered through silica.

Colourless oil. Yield: 65%.

$^1$H [lacuna] NMR (CDCL$_3$, 250 MHz): 1.28 (6H, s), 1.30 (6H, s), 1.77 (4H, s), 4.53 (2H, d, J=5.4 Hz), 5.29 (1H, s), 5.43 (1H, s), 7.21 (1H Ar, dd, J=1.9 Hz, J=8.2 Hz), 7.29 (1H Ar, d, J=8.2 Hz), 7.38 (1H Ar, d, J=1.9 Hz).

i) 6-(1-bromomethylvinyl)-1,1,4,4-tetramethyl-1,2,3,4-tetrahydronaphthalene

Tetrabromomethane (1.21 g, 3.8 mmol) is added to a mixture of triphenylphosphine (970 mg, 3.8 mmol) in ethyl ether (20 ml). A solution of 2-(5,5,8,8-Tetramethyl-5,6,7,8-tetrahydronaphthalen-2-yl)prop-2-en-1-ol (300 mg, 1.2 mmol) in ethyl ether (2 ml) is added. Stirring is continued for 24 h, then the reaction mixture is treated with water and ethyl acetate. The organic phase is washed with water and then concentrated in vacuo in a rotary evaporator. The oil obtained is taken up in heptane and filtered through silica. The filtrate is concentrated in vacuo in a rotary evaporator.

Yellow oil. Yield: quantitative.

$^1$H [lacuna] NMR (CDCL$_3$, 250 MHz); 1.28 (6H, s), 1.31 (6H, s), 1.78 (4H, s), 4.37 (2H, s), 5.44 (1H, s), 5.55 (1H, s), 7.23 to 7.28 (2H Ar, m), 7.44 (1H Ar, s).

j) Methyl 3-iodo-4-[2-(5,5,8,8-tetramethyl-5,6,7,8-tetrahydronaphthalen-2-yl)allylsulphanyl]-benzoate 75% NaH (115 mg, 3.58 mmol) is added to a solution of methyl 3-Iodo-4-mercaptobenzoate (531 mg, 3.25 mmol) in DMF (20 ml) at 0° C. Stirring is continued for 20 min at ambient temperature, then a solution of 6-(1-bromomethylvinyl)-1,1,4,4-tetramethyl-1,2,3,4-tetrahydronaphthalene (1 g, 3.25 mmol) in DMF (5 ml) is added dropwise. The mixture is stirred for 2 h at ambient temperature, and treated with an aqueous hydrochloric acid solution and ethyl ether. The organic phase is washed twice with water, dried over magnesium sulphate, and concentrated in vacuo at 40° C. in a rotary evaporator. The product is purified by flash chromatography on a silica column (CH$_2$Cl$_2$ 50% heptane 50%).

White solid. Mass: 680 mg, Yield: 54%. M.p.=142° C. $^1$H (lacuna] NMR (CDCL$_3$, 250 MHz): 1.28 (6H, s), 1.30 (6H, s), 1.69 (4H, s), 3.89 (3H, s), 4.02 (2H, s), 5.37 (1H, s), 5.51 (1H, s), 7.18 (1H Ar, d, J=8.3 Hz), 7.21 to 7.31 (2H Ar, m), 7.39 (1H Ar, d, J=1.7 Hz), 7.91 (1H Ar, dd, J=8.3 Hz, J=1.7 Hz), 8.43 (1H Ar, d, J=1.7 Hz).

$^{13}$C [lacuna] NMR (CDCL$_3$, 250 MHz): 32.1, 32.2, 34.5, 34.7, 35.3, 35.4, 38.9, 52.6, 97.5, 115.9, 123.6, 124.5, 126.2, 127.0, 128.2, 129.7, 136.8, 140.5, 141.8, 145.3, 145.4, 148.7, 165.8.

k) methyl 3-methyl-3-(5,5,8,8-tetramethyl-5,6,7,5-tetrahydronaphthalen-2-yl)-2,3-dihydrobenzo[b]thiophene-5-carboxylate.

A mixture of tributhylamine (881 ul, 3.7 mmol), tetrakis (triphenylphosphine)palladium (367 mg, 0.32 mmol), formic acid (63 ul, 1.7 mmol) and methyl 3-Iodo-4-[2-(5,5,8,8-tetramethyl-5,6,7,8-tetrahydronaphthalen-2-yl)allylsulphanyl]benzoate (655 mg, 1.7 mmol) in acetonitrile (25 ml) is heated at 80° C. for 4 h. The reaction mixture is concentrated in vacuo at 40° C. in a rotary evaporator treated with water and ethyl ether. After separation, the organic phase is washed twice with water, dried over magnesium sulphate, and concentrated in vacuo at; 40° C. in a rotary evaporator. The product is purified by flash chromatography on a silica column (CH$_2$Cl$_2$ 50% heptane 50%)

Colourless oil. Mass: 121 mg, Yield: 19%.

$^1$H [lacuna] NMR (CDCL$_3$, 250 MHz): 1.19 (3H, s), 1.23 (3H, s), 1.26 (6H, s), 1.66 (4H, s), 1.76 (3H, s), 3.39 (1H, d, J=11 Hz), 3.64 (1H, d, J=11 Hz), 3.84 (3H, s), 6.93 (1H Ar, dd, J=2 Hz, J=8.4 Hz), 7.19 to 7.24 (2H Arm), 7.29 (1H Ar, d, J=8.1 Hz), 7.55 (1H Ar, d, J=1.6 Hz), 7.85 (1H Ar, dd, J=1.7, J=8.1 Hz).

$^{13}$C [lacuna] NMR (CDCL$_3$, 250 MHz): 26.38, 32.3, 32.4, 34.40, 34.8, 35.5, 35.6, 49.7, 52.3, 55.2, 122.4, 124.4, 125.1, 126.6, 126.9, 127.0, 129.7, 143.1, 143.8, 145.1, 148.4, 148.6, 167.4.

l) 3-methyl-3-(5,5,8,8-tetramethyl-5,6,7,8-tetrahydronaphthalen-2-yl)-2,3-dihydrobenzo[b]thiophene-5-methanol.

A 1M diisobutylaluminium hydride solution in toluene (0.67 ml, 0.67 mmol) is added at 0° C., dropwise, to a solution of methyl 3-methyl-3-(5,5,8,8-tetramethyl-5,6,7,8-tetrahydronaphthalen-2-yl)-2,3-dihydrobenzo[b]thiophene-5-carboxylate (121 mg, 0.31 mmol) in toluene (5 ml). The solution is stirred for 2 h at 0° C., and then treated with a solution of double tartrate of sodium and potassium filtered and taken up in a mixture of ethyl ether and water. The organic phase is washed with water, dried over magnesium sulphate and concentrated in vacuo at 40° C. in a rotary evaporator.

Colourless oil. Mass: 120 mg, Yield: quantitative.

m) 3-methyl-3-(5,5,8,8-tetramethyl-5,6,7,8-tetrahydronaphthalen-2-yl)-2,3-dihydrobenzo[b]thiophene-5-carbaldehyde.

A mixture of alcohol obtained above (120 mg, 0.31 mmol), manganese (IV) oxide (270 mg, 3.1 mmol) in dichloromethane (5 ml) is stirred at ambient temperature for 3 h. The manganese oxide is removed by filtration through silica. The product is obtained by concentration in vacuo at 40° C. in a rotary evaporator.

White solid. Mass: 100 mg, Yield: 88a. M.p.=143° C.

$^1$H [lacuna] NMR (CDCL$_3$, 250 MHz): 1.11 (3H, s), 1.17 (3H, s), 1.20 (GH, s), 1.60 (4H, s), 1.79 (3H, s), 3.32 (1H, d, J=11.3 Hz), 3.63 (1H, d, J=11.3 Hz), 6.93 (1H Ar, dd, J=2.2 Hz, J=8.2 Hz), 7.14 to 7.18 (2H Ar, m.), 7.28 (1–8, d, J=15 Hz), 7.31 (1H Ar, d, J=B Hz), 7.59 (1H Ar, dd, J=1.5, J=8 Hz), 9.76 (1H, s).

n) ethyl 3-[3-methyl-3-(5,5,8,8-tetramethyl-5,6,7,8-tetrahydronaphthalen-2-yl)-2,3-dihydrobenzo-[b] thiophen-5-yl]acrylate.

The experimental procedure is analogous to that followed for Example 1i applied to 3-Methyl-3-(5,5,8,8-tetramethyl-5,6,7,8-tetrahydronaphthalen-2-yl)-2,3-dihydrobenzo[b] thiophene-5-carbaldehyde. The product is purified by filtration on silica (CH$_2$Cl$_2$)

Colourless oil. Mass: 115 mg, Yield: quantitative.

$^1$H [lacuna] NMR (CDCL$_3$, 250 MHz): 1.19 to 1.33 (15H, m), 1.67 (4H, s), 1.74 (3H, s), 3.35 (1H, d, J=11 Hz), 3.65 (1H, d, J=11 Hz), 4.22 (2H, q, J=7.1 Hz), 6.27 (1H, d, J=15.9 Hz), 6.99 to 7.03 (2H Ar, m), 7.21 to 7.27 (3H Ar, m), 7.33 (1H Ar, d, J=8.1 Hz), 7.57 (1H, dd, J=1.5, J=8 Hz).

Example 24

3-[3-Methyl-3-(5,5,8,8-tetramethyl-5,6,7,8-tetrahydronaphthalen-2-yl)-2,3-dihydrobenzo[b]thiophen-5-yl]acrylic acid.

The experimental procedure is analogous to that followed for Example 9 applied to ethyl 3-[3-methyl-3-(5,5,8,8-tetramethyl-5,6,7,8-tetrahydronaphthalen-2-yl)-2,3-dihydrobenzo[b]thiophen-5-yl]acrylate.

White solid. Mass: 70 mg, Yield: 75%. M.p.=196° C.

$^1$H [lacuna] NMR (CDCL$_3$, 250 MHz): 1.19 (3H, s), 1.25 (3H, s), 1.27 (6H, s), 1.67 (4H, s), 1.75 (3H, s), 3.35 (1H, d, J=11.2 Hz), 3.66 (1H, d, J=11.2 Hz), 6.26 (1H, d, J=15.9 Hz), 7.00 to 7.03 (2H Ar, m), 7.21 to 7.37 (4H Ar, m), 7.67 (1H Ar, d, J=15.9 Hz).

Example 25 ethyl 3-[3-(5,6,7,8-tetrahydro-5,5,8,8-tetramethyl-2-naphthyl)-7-methoxy-3-methyl-2,3-dihydrobenzofuran-5-yl]acrylate a) 3-Iodo-5-methoxy-4-[2-(5,5,8,8-tetramethyl-5,6,7,8-tetrahydronaphthalen-2-yl)allyloxy]-benzaldehyde.

The experimental procedure is analogous to that followed for Example 23j applied to 5-iodovanilin and to 6-(1-bromomethylvinyl)-1,1,4,4-tetramethyl-1,2,3,4-tetrahydronaphthalene. The product is purified by flash chromatography on a silica column (CH$_2$Cl$_2$ 50% heptane 50%).

Yellow solid. Mass: 1.05 g, Yield: 65%. M.p.=75° C.

$^1$H [lacuna] NMR (CDCL$_3$, 250 MHz): 1.28 (6H, s), 1.29 (6H, s), 1.69 (4H, s), 3.91 (3H, s), 4.99 (2H, s), 5.55 (1H, s), 5.59 (1H, s), 7.29 (2H Ar, s), 7.41 to 7.45 (2H Ar, m), 7.84 (1H Ar, d, J=1.8 Hz), 9.83 (1H s).

b) 3-(5,6,7,8-tetrahydro-5,5,8,8-tetramethyl-2-naphthyl)-7-methoxy-3-methyl-2,3-dihydrobenzofuran-5-carbaldehyde.

The experimental procedure is analogous to that followed for Example 1e applied to 3-Iodo-5-methoxy-4-[2-(5,5,8,8-tetramethyl-5,6,7,8-tetrahydronaphthalen-2-yl) allyloxy] benzaldehyde. The product is purified by flash chromatography on a silica column (CH$_2$Cl$_2$ 50% heptane 50%).

Yellow oil. Mass: 500 mg, Yield: 67%.

$^1$H [lacuna] (CDCl$_3$): 1.20 to 1.26 (12H, m), 1.67 (4H, s), 1.77 (3H, s), 3.98 (3H, s), 4.64 (1H, d, J=8.9 Hz), 4.77 (1H, d, J=8.9 Hz), 6.99 (1H, dd, J=2.2 Hz, J=8.2 Hz), 7.20 to 7.26 (3H Ar, m), 7.37 (1H Ar, d, J=1.3 Hz), 9.79 (1H, s).

c) ethyl 3-[3-(5,6,7,8-tetrahydro-5,5,8,8-tetramethyl-2-naphthyl)-7-methoxy-3-methyl-2,3-dihydrobenzofuran-5-yl) acrylate The experimental procedure is analogous to that followed for Example 1i applied to 3-(5,6,7,8-tetrahydro-5,5,8,8-tetramethyl-2-naphthyl)-7-methoxy-3-methyl-2,3-dihydrobenzofuran-5-carbaldehyde. The product is purified by filtration on silica (CH$_2$Cl$_2$).

Colourless oil. Mass: 420 mg, Yield: 71%.

$^1$H [lacuna] (CDCl$_3$): 1.21 to 1.33 (15H, m), 1.67 (4H, s), 1.73 (3H, s), 3.94 (3H, s), 4.23 (2H, q, J=7.1 Hz), 4.55 (1H, d, J=8.8 Hz), 4.69 (1H, d, J=8.8 Hz), 6.26 (1H, d, 15.9 Hz), 6.85 (1H Ar, s), 6.96 to 7.02 (2H Ar, m), 7.20 to 7.26 (2H Ar, m), 7.60 (1H Ar, d, J=15.9 Hz).

Example 26

3-[3-(5,6,7,8-Tetrahydro-5,5,8,8-tetramethyl-2-naphthyl)-7-methoxy-3-methyl-2,3-dihydrobenzofuran-5-yl]acrylic acid.

The experimental procedure is analogous to that followed for Example 9 applied to ethyl 3-[3-(5,6,7,8-tetrahydro-5,5,8,8-tetramethyl-2- naphthyl)-7-methoxy-3-methyl-2,3-dihydrobenzofuran-5-yl]acrylate. The product is purified by crystallization.

White solid. Mass: 350 mg, Yield: 89%. M.p.=55° C.

$^1$H [lacuna] (CDCl$_3$): 1.21 to 1.26 (12H, m), 1.67 (4H, s), 1.74 (3H, s), 3.95 (3H, s), 4.57 (1H, d, J=8.8 Hz), 4.70 (1H, d, J=8.8 Hz), 6.25 (1H, d, 15.9 Hz), 6.88 (1H Ar, s), 6.99 to 7.03 (2H Ar, m), 7.21 to 7.26 (2H Ar, m), 7.69 (1H Ar, d, J=15.9 Hz).

Example 27

N-(4-hydroxyphenyl)-3-[7-methoxy-3-methyl-3-(5,5,8,8-tetramethyl-5,6,7,8-tetrahydronaphthalen-2-yl)-2,3-dihydrobenzofuran-5-yl]acrylamide A solution of 3-[3-(5,6,7,8-tetrahydro-5,5,8,8-tetramethyl-2-naphthyl)-7-methoxy-3-methyl-2,3-dihydrobenzofuran-5-yl]acrylic Acid (150 mg, 0.357 mmol), 1-hydroxybenzotriazole (96 mg, 0.714 mmol), 1,3-dicyclohexylcarbodiimide (147 mg, 0.714 mmol) and 4-aminophenol (39 mg, 0.357 mmol) in 5 ml of THF and 5 ml of DMF is stirred at ambient temperature for 15 hours. Water and ethyl acetate are added. After stirring and separation, the aqueous phase is extracted with ethyl acetate. The organic phases are then combined and washed twice with water, then dried over magnesium sulphate and concentrated in vacuo at 40° C. in a rotary evaporator. The product is then purified by flash chromatography on a silica column (heptane 50%, ethyl acetate 50%)

White solid. Mass 70 mg. Yield 37%. M.p.=80° C.

$^1$H [lacuna] (CDCl$_3$): 1.21 to 1.25 (12H, m), 1.66 (4H, s), 1.73 (3H, s), 3.92 (3H, s), 4.54 (1H, d, J=8.8 Hz), 4.67 (1H, d, J=8.8 Hz), 6.34 (1H, d, 15.4 Hz), 6.77 (2H Ar, d, J=8.7 Hz), 6.87 (1H Ar, s), 6.94 (1H Ar, s), 7.01 (1H Ar, d, J=8.2 Hz), 7.20 to 7.24 (2H Ar, m), 7.32 to 7.36 (2H Ar, m), 7.63 (1H Ar, d, J=15.4 Hz).

B. FORMULATION EXAMPLES

1) Oral Route (a) The following composition is prepared in the form of a 0.8 g tablet

| | |
|---|---|
| Compound of Example 1 | 0.005 g |
| Pregelatinized starch | 0.265 g |
| Microcrystalline cellulose | 0.300 g |
| Lactose | 0.200 g |
| Magnesium stearate | 0.030 g |

For the treatment of acne, 1 to 3 tablets per day will be administered to an adult individual for 3 to 6 months according to the seriousness of the case treated.

(b) A drinkable suspension is prepared which is intended to be packaged in 5 ml ampoules

| | |
|---|---|
| Compound of Example 2 | 0.050 g |
| Glycerol | 0.500 g |
| 70% sorbitol | 0.500 g |
| Sodium saccharinate | 0.010 g |
| Methyl parahydroxybenzoate | 0.040 g |
| Flavour q.s. | |
| Purified water q.s.p. | 5 ml |

For the treatment of acne, 1 ampoule per day will be administered to an adult individual for 3 months according to the seriousness of the case treated.

(c) The following formulation intended to be packaged in gelatin capsules is prepared:

| | |
|---|---|
| Compound of Example 1 | 0.025 g |
| Corn starch | 0.060 g |
| Lactose q.s. | 0.300 g |

The gelatin capsules used are composed of gelatin, titanium oxide and a preservative.

In the treatment of psoriasis, 1 gelatin capsule per day will be administered to an adult individual for 30 days.

2) Topical Route (a) The following non-ionic water-in-oil cream is prepared:

| | |
|---|---|
| Compound of Example 2 | 0.100 g |
| Mixture of emulsive lanolin alcohols, waxes and refined oils, sold by BDF under the name "Eucerine anhydre" | 39.900 g |
| Methyl parahydroxybenzoate | 0.075 g |
| Propyl parahydroxybenzoate | 0.075 g |
| Sterile demineralized water q.s. | 100.000 g |

This cream will be applied to a psoriatic skin 1 to 2 times per day for 30 days.

(b) A gel is prepared by carrying out the following formulation:

| | |
|---|---|
| Compound of Example 1 | 0.050 g |
| Erythromycin base | 4.000 g |
| Butylhydroxytoluene | 0.050 g |
| Hydroxypropylcellulose sold by Hercules under the name of "KLUCEL HF" | 2.000 g |
| Ethanol (95°) q.s. | 100.000 g |

This gel will be applied to a skin suffering from dermatosis or a skin with acne 1 to 3 times per day for 6 to 12 weeks according to the seriousness of the case treated.

(c) An antiseborrhoeic lotion is prepared by proceeding with the mixture of the following ingredients:

| | |
|---|---|
| Compound of Example 2 | 0.030 g |
| Propylene glycol | 5.000 g |
| Butylhydroxytoluene | 0.100 g |
| Ethanol (95°) q.s. | 100.000 g |

This lotion will be applied two times per day to a seborrhoeic scalp and a significant improvement is noted within a period of between 2 and 6 weeks.

(d) A cosmetic composition against the harmful effects of the sun is prepared by proceeding with the mixture of the following ingredients:

| | |
|---|---|
| Compound of Example 1 | 1.000 g |
| Benzylidene camphor | 4.900 g |
| Fatty acid triglycerides | 31.000 g |
| Glyceryl monostearate | 6.000 g |
| Stearic acid | 2.000 g |
| Cetyl alcohol | 1.200 g |
| Lanolin | 4.000 g |
| Preservatives | 0.300 g |
| Propylene glycol | 2.000 g |
| Triethanolamine | 0.500 g |
| Perfume | 0.400 g |
| Demineralized water q.s. | 100.000 g |

This composition will be applied daily, it allows light-induced aging to be combated, (e) The following non-ionic oil-in-water cream is prepared:

| | |
|---|---|
| Compound of Example 2 | 0.500 g |
| Vitamin D3 | 0.020 g |
| Cetyl alcohol | 4.000 g |
| Glyceryl monostearate | 2.500 g |
| PEG 50 stearate | 2.500 9 |
| Shea butter | 9.200 g |
| Propylene glycol | 2.000 g |
| Methyl parahydroxybenzoate | 0.075 g |
| Propyl parahydroxybenzoate | 0.075 g |
| Sterile demineralized water q.s. | 100.000 g |

This cream will be applied to a psoriatic skin 1 to 2 times per day for 30 days.

(f) A topical gel is prepared by proceeding with the mixture of the following ingredients:

| | |
|---|---|
| Compound of Example 1 | 0.050 g |
| Ethanol | 43.000 g |
| α-Tocopherol | 0.050 g |
| Carboxyvinyl polymer sold under the name "Carbopol 941" by "Goodrich" | 0.500 g |
| Triethanolamine in 20% by weight aqueous solution | 3.800 g |
| Water | 9.300 g |
| Propylene glycol qs | 100.000 g |

This gel will be applied in the treatment of acne 1 to 3 times per day for 6 to 12 weeks according to the seriousness of the case treated.

(g) An anti-hair loss hair lotion and lotion for the regrowth of the hair is prepared by proceeding with the mixture of the following ingredients:

| | |
|---|---|
| Compound of Example 2 | 0.05 g |
| Compound sold under the name "Minoxidil" | 1.00 g |
| Propylene glycol | 20.00 g |
| Ethanol | 34.92 g |
| Polyethylene glycol (molecular mass = 400) | 40.00 g |
| Butylhydroxyanisole | 0.01 g |
| Butylhydroxytoluene | 0.02 g |
| Water qs | 100.00 g |

This lotion will be applied 2 times per day for 3 months to a scalp which has undergone a significant loss of hair.

(h) An anti-acne cream is prepared by proceeding with the mixture of the following ingredients:

| | |
|---|---|
| Compound of Example 1 | 0.050 g |
| Retinoic acid | 0.010 g |
| Mixture of glyceryl stearates and of polyethylene glycol (75 mol) sold under the name of "Gelot 64" by "GATTEFOSSE" | 15.000 g |
| Kernel oil polyoxyethylenated with 6 mol of ethylene oxide sold under the name of "Labrafil M2130 CS" by "GATTEFOSSE" | 8.000 g |
| Perhydrosqualene | 10.000 g |
| Preservatives | qs |
| Polyethylene glycol (molecular mass = 400) | 8.000 g |
| Disodium salt of ethylendiaminetetra-acetic acid | 0.050 g |
| Purified water qs | 100.000 g |

This cream will be applied to a skin suffering from dermatitis or a skin with acne 1 to 3 times per day for 6 to 12 weeks.

(i) An oil-in-water cream is prepared by producing the following formulation:

| | |
|---|---|
| Compound of Example 1 | 0.020 g |
| Betamethasone 17-valerate | 0.050 g |
| S-Carboxymethylcysteine | 3.000 g |
| Polyoxyethylene stearate (40 mol of ethylene oxide) sold under the name of "Myrj 52" by "ATLAS" | 4.000 g |
| Sorbitan monolaurate, polyoxyethylenated with 20 mol of ethylene oxide sold under the name of "Tween 20" by "ATLAS" | 1.800 g |
| Mixture of mono and distearate of glycerol sold under the name of "Géléol" by "GATTEFOSSE" | 4.200 g |
| Propylene glycol | 10.000 g |
| Butylhydroxyanisole | 0.010 g |
| Butylhydroxytoluene | 0.020 g |
| Cetostearyl alcohol | 6.200 g |

-continued

| Preservatives | q.s. |
|---|---|
| Perhydrosqualene | 18.000 g |
| Mixture of caprylic/capric triglycerides sold under the name of "Miglyol 812" by "DYNAMIT NOBEL" | 4.000 g |
| Triethanolamine (99% by weight) | 2.500 g |
| Water q.s. | 100.000 g |

This cream will be applied 2 times per day for 30 days on a skin suffering from dermatitis.

(j) The following oil-in-water type cream is prepared:

| Lactic acid | 5.000 g |
|---|---|
| Compound of Example 1 | 0.020 g |
| Polyoxyethylene stearate (40 mol of ethylene oxide) sold under the name of "Myrj 52" by "ATLAS" | 4.000 g |
| Sorbitan monolaurate, polyoxyethylenated with 20 mol of ethylene oxide sold under the name of "Tween 20" by "ATLAS" | 1.800 g |
| Mixture of mono and distearate of glycerol sold under the name of "Geleol" by "GATTEFOSSE" | 4.200 g |
| Propylene glycol | 10.000 g |
| Butylhydroxyanisole | 0.010 g |
| Butylhydroxytoluene | 0.020 g |
| Cetostearyl alcohol | 6.200 g |
| Preservatives | q.s. |
| Perhydrosqualene | 18.000 g |
| Mixture of caprylic/capric triglycerides sold under the name of "Miglyol 812" by "DYNAMIT NOBEL" | 4.000 g |
| Water q.s. | 100.000 g |

This cream will be applied 1 time per day, it helps to combat aging whether it is light-induced or chronological.

We claim:

1. A compound having the following general formula (I)

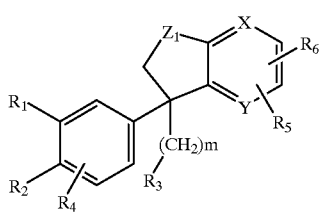

(I)

in which:

$Z_1$ is O or S,

X and Y are CH, $R_1$ and $R_2$ taken together form, with the adjacent aromatic ring, a ring with 5 or 6 members which is optionally substituted by methyl groups and/or optionally interrupted by an SO radical, an $SO_2$ radical, or an oxygen or sulphur atom, $R_3$ is:
(i) a hydrogen atom, a lower alkyl radical, a lower alkenyl radical, a lower alkynyl radical, an aryl radical, a monohydroxyalkyl or polyhydroxyalkyl radical, a polyether radical, a cyano radical or an —O—$R_7$ radical, (ii) a radical of formula:

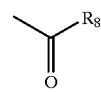

or (iii) a radical of formula

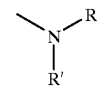

$R_4$ is:
(i) a hydrogen atom,
(ii) a lower alkyl radical,
(iii) a halogen atom,
(iv) an —$OR_7$ radical, $R_5$ is:
(i) a radical of formula:

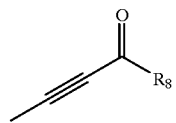

(ii) a radical of formula:

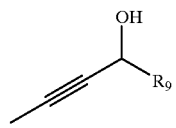

(iii) a radical of formula:

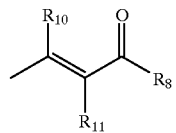

(iv) a radical of formula:

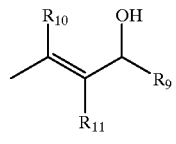

(v) a radical of formula:

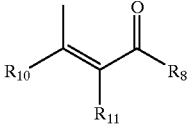

(vi) a radical of formula:

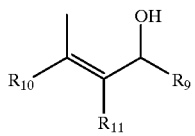

$R_6$ is a hydrogen atom, a halogen atom, a lower alkyl radical of the —$OR_7$ radical, $R_7$, is a hydrogen atom, a lower alkyl radical, an aryl radical, an aralkyl radical, optionally substituted, a monohydroxyalkyl or polyhydroxyalkyl radical, a polyether radical or a lower acyl radical, $R_8$ is:
(a) a hydrogen atom, a lower alkyl radical,
(b) a radical of formula:

R and R' having the meaning given below,
(c) an —$OR_{12}$ radical
(d) a sugar or amino acid side chain, $R_9$ is a hydrogen atom, or a lower alkyl radical, $R_{10}$, and $R_{11}$, which are identical or different, are a hydrogen atom or a lower alkyl radical, $R_{12}$ is a hydrogen atom, a lower alkyl radical, a mono- or polyhydroxyalkyl radical, an optionally substituted aryl or aralkyl radical, R and R' which are identical or different, are protective groups of amine, a hydrogen atom, a lower alkyl radical or alternatively, taken together, form a heterocycle, m is equal to 0 or 1, and the optical and geometric isomers of the said compounds of formula (I) as well as their salts.

2. A salt comprising a compound according to claim 1, wherein said salt is selected from the group consisting of alkali metal, alkaline earth metal, zinc, organic amine, mineral acid, and organic acid salts.

3. The compound of claim 1, wherein the lower alkyl radicals are selected from the group consisting of methyl, ethyl, isopropyl, butyl, tertiary butyl and hexyl radicals.

4. The compound of claim 1, wherein the lower alkenyl radicals are radicals having from 2 to 6 linear or branched carbon atoms forming one or more double bonds.

5. The compound of claim 1, wherein the lower alkynyl radicals are radicals having from 3 to 6 linear or branched carbon atoms forming one or several triple bonds.

6. The compound of claim 1, wherein the lower acyl radical is a radical having from 1 to 6 carbon atoms.

7. The compound of claim 1, wherein the polyhydroxyalkyl radicals are selected from the group consisting of 2,3-dihydroxypropyl, 2,3,4-trihydroxybutyl and 2,3,4,5-tetrahydroxypentyl radicals, and the pentaerythritol side chain.

8. The compound of claim 1, wherein the optionally substituted aryl radicals are a phenyl radical, optionally substituted by one or more halogen atoms, a hydroxyl group, a methoxy group or an optionally substituted amine group.

9. The compound according to claim 1, wherein the optionally substituted aralkyl radicals are chosen from benzyl radical and phenethyl radical, optionally substituted by one or more halogen atoms, a hydroxyl or nitro function, or a methoxy group.

10. The compound of claim 1, wherein the sugar side chains are selected from the group consisting of the glucose, galactose, mannose and glucuronic acid side chains.

11. The compound of claim 1, wherein the amino acid side chains are selected from the group consisting the side chains derived from lysine, glycine and aspartic acid.

12. The compound of claim 1, wherein the heterocyclic radicals are selected from the group consisting of piperidino, morpholino, pyrrolidino, and piperazino radicals, optionally substituted at position 4 by $C_1$–$C_6$ alkyl radical or by a mono or polyhydroxyalkyl.

13. The compound of claim 1, wherein the polyether radicals are selected from the group consisting of the methoxymethyl ether, methoxyethoxymethyl ether and methylthiomethyl ether radicals.

14. The compound of claim 1, which are taken, alone or as a mixture, from the group consisting of:

ethyl 3-[3-(5,6,7,8-tetrahydro-5,5,8,8-tetramethyl-2-naphthyl)-3-methyl-2,3-dihydrobenzofuran-5-yl]-acrylate, 3-[3-(5,6,7,8-tetrahydro-5,5,8,8-tetramethyl-2-naphthyl)-3-methyl-2,3-dihydrobenzofuran-5-yl]acrylic acid,

[3-methyl-3-(5,5,8,8-tetramethyl-5,6,7,8-tetrahydronaphthalen-2-yl)-2,3-dihydrobenzofuran-5-yl]pronynoic acid, ethyl (+)-3-[3-methyl-3-(5,5,8,8-tetramethyl-5,6,7,8-tetrahydronaphthalen-2-yl)-2,3-dihydrobenzofuran-5-yl]-acrylate, (+)-3-[3-methyl-3-(5,5,8,8-tetramethyl-5,6,7,8-tetrahydronaphthalen-2-yl)-2,3-dihydrobenzofuran-5-yl]-acrylic acid, ethyl (−)-3-[3-methyl-3-(5,5,8,8-tetramethyl-5,6,7,8-tetrahydronaphthalen-2-yl)-2,3-dihydrobenzofuran-5-yl]-acrylate, (−)-3-[3-Methyl-3-(5,5,8,8-tetramethyl-5,6,7,8-tetrahydronaphthalen-2-yl)-2,3-dihydrobenzofuran-5-yl]-acrylic acid, ethyl 3-[3-methyl-3-(3,5,5,8,8-pentamethyl-5,6,7,8-tetrahydronaphthalen-2-yl)-2,3-dihydrobenzofuran-5-yl]-acrylate, 3-[3-methyl-3-(3,5,5,8,8-pentamethyl-5,6,7,8-tetrahydronaphthalen-2-yl)-2,3-dihydrobenzofuran-5-yl]-acrylic acid, ethyl 3-[3-methyl-3-(naphthalen-2-yl)-2,3-dihydrobenzofuran-5-yl]acrylate, 3-[3-methyl-3-(naphthalen-2-yl)-2,3-dihydrobenzofuran-5-yl]acrylic acid, ethyl 3-[3-(8,8-dimethyl-5,6,7,8-tetrahydronaphthalen-2-yl)-3-methyl-2,3-dihydrobenzofuran-5-yl]acrylate, 3-[3-(8,8-dimethyl-5,6,7,8-tetrahydronaphthalen-2-yl)-3-methyl-2,3-dihydrobenzofuran-5-yl]acrylic acid, ethyl 3-[3-(5,5-dimethyl-5,6,7,8-tetrahydronaphthalen-2-yl)-3-methyl-2,3-dihydrobenzofuran-5-yl]acrylate, 3-[3-(5,5-dimethyl-5,6,7,8-tetrahydronaphthalen-2-yl)-3-methyl-2,3-dihydrobenzofuran-5-yl]acrylic acid, ethyl 3-[3-methyl-3-(5,5,8,8-tetramethyl-5,6,7,8-tetrahydronaphthalen-2-yl)-2,3-dihydrobenzofuran-6-yl]-acrylate, 3-[3-methyl-3-(5,5,8,8-tetramethyl-5,6,7,8-tetrahydronaphthalen-2-yl)-2,3-dihydrobenzofuran-6-yl]acrylic acid, ethyl 3-[3-allyl-3-(5,5,8,8-tetramethyl-5,6,7,8-tetrahydronaphthalen-2-yl)-2,3-dihydrobenzofuran-5-yl]-acrylate, 3-[3-allyl-3-(5,5,8,8-tetramethyl-5,6,7,8-tetrahydronaphthalen-2-yl)-2,3-dihydrobenzofuran-5-yl]acrylic acid, methyl (E)-3-[3-methyl-3-(5,5,8,8-tetramethyl-5,6,7,8-tetrahydronaphthalen-2-yl)-2,3-dihydrobenzofuran-5-yl]-but-2-enaote, methyl (Z)-3-[3-methyl-3-(5,5,8,8-tetramethyl-5,6,7,8-tetrahydronaphthalen-2-yl)-2,3-dihydrobenzofuran-5-yl]-but-2-enoate, (E)-3-[3-methyl-3-(5,5,8,8-tetramethyl-5,6,7,8-tetrahydronaphthalen-2-yl)-2,3-dihydrobenzofuran-5-yl]but-2-enoic acid, ethyl 3-[3-methyl-3-(5,5,8,8-tetramethyl-5,6,7,8-tetrahydronaphthalen-2-yl)-2,3-dihydrobenzo[b]thiophen-5-yl]acrylate, 3-[3-methyl-3-(5,5,8,8-tetramethyl-5,6,7,8-tetrahydronaphthalen-2-yl)-2,3-dihydrobenzo[b]thiophen-5-yl]-acrylic acid, ethyl 3-[3-(5,6,7,8-tetrahydro-5,5,8,8-tetramethyl-2-naphthyl)-7-methoxy-3-methyl-2,3-dihydrobenzofuran-5-yl]acrylate)

3-[3-(5,6,7,8-tetrahydro-5,5,8,8-tetramethyl-2-naphthyl)-7-methoxy-3-methyl-2,3-dihydrobenzofuran-5-yl] acrylic acid, or N-(4-hydroxyphenyl)-3-[7-methoxy-3-methyl-3-(5,5,8,8-tetramethyl-5,6,7,8-tetrahydronaphthalen-2-yl)-2,3-dihydrobenzofuran-5-yl]acrylamide.

15. The compound of claim 1, having at least one of the following characteristics:

$R_1$ and $R_2$, taken together, form an aromatic ring such as described in claim 1, $R_3$ is a hydrogen, a lower alkenyl radical, a lower alkyl radical or an —$OR_7$ radical $R_4$ is a hydrogen, $R_5$ is a radical or formula (i) or (iii), $R_6$ is a hydrogen, $R_8$ is an $OR_{12}$ radical, X and Y are Cr, $Z_1$ is an oxygen or sulphur atom.

16. A pharmaceutical composition comprising pharmaceutically acceptable carrier and at least one compound as defined in claim 1.

17. The composition of claim 16 wherein the concentration of the compound(s) is between 0.001% and 5% by weight with respect to the whole of the composition.

18. A method for the treatment of a condition selected from the group consisting of dermatological conditions affecting differentiation and proliferation related keratinization disorders; inflammatory and immunoallergic related keratinization disorders; cutaneous, mucous, ungual, and arthropathic psoriasis; cutaneous and respiratory atopy; gingival hypertrophy; inflammatory conditions without a keratinization disorder; viral, non viral, benign and malignant dermal and epidermal proliferations; ultra-violet radiation induced proliferations; bullosis and collagen diseases; ophthalmological disorders; aging of the skin; the stigmata of epidermal and dermal atrophy induced by local and systemic corticosteroids; cicatrization disorders and vibices; cicatrization, sebaceous function disorders; cancerous and precancerous states; inflammatory disorders; alopecia; immune related dermatological disorders; disorders of the cardiovascular system, non-insulin dependent diabetes related cutaneous disorders; which method comprises administering an effective amount of the compound of claim 1 to a patient in need of such treatment.

19. A method for the prevention or treatment of dermatological conditions affecting differentiation and proliferation related keratinization disorders, said method comprising administering an effective amount of the compound of claim 1 to a patient in need of such prevention or treatment.

20. A method for the prevention of a condition selected from the group consisting of the stigmata of epidermal and dermal atrophy induced by local and systemic corticosteroids; and cicatrization disorders and vibices; which method comprises administering an effective amount of the compound of claim 1 to a patient in need of such prevention.

21. A method for inhibiting a condition selected from the group consisting of the stigmata of epidermal and dermal atrophy induced by local and systemic corticosteroids; cicatrization disorders and vibices; and alopecia; which method comprises administering an effective amount of the compound of claim 1 to a patient in need of such inhibition.

* * * * *